(12) United States Patent
Coffey

(10) Patent No.: US 7,910,791 B2
(45) Date of Patent: Mar. 22, 2011

(54) COMBINATION SIS AND VACUUM BANDAGE AND METHOD

(76) Inventor: Arthur C. Coffey, Carmel, IN (US)

( * ) Notice: Subject to any disclaimer, the term of this patent is extended or adjusted under 35 U.S.C. 154(b) by 1667 days.

(21) Appl. No.: 10/276,778

(22) PCT Filed: May 15, 2001

(86) PCT No.: PCT/US01/15611
§ 371 (c)(1),
(2), (4) Date: Nov. 18, 2002

(87) PCT Pub. No.: WO01/89431
PCT Pub. Date: Nov. 29, 2001

(65) Prior Publication Data
US 2003/0208149 A1    Nov. 6, 2003

Related U.S. Application Data

(62) Division of application No. 09/855,287, filed on May 15, 2001.

(60) Provisional application No. 60/206,226, filed on May 22, 2000.

(51) Int. Cl.
*A61F 5/00* (2006.01)
*A61F 13/00* (2006.01)
*A61K 9/70* (2006.01)
*A61L 15/00* (2006.01)
*A61H 7/00* (2006.01)
*A61M 35/00* (2006.01)

(52) U.S. Cl. ............ 602/48; 602/41; 602/42; 602/43; 424/443; 424/445; 604/304; 604/305; 604/306; 604/313; 601/6

(58) Field of Classification Search ............ 602/41–59; 604/305, 304, 307, 313; 424/443–449
See application file for complete search history.

(56) References Cited

U.S. PATENT DOCUMENTS

| | | |
|---|---|---|
| 774,529 A | 11/1904 | Nieschang |
| 1,000,001 A | 8/1911 | Holz |
| 1,355,846 A | 10/1920 | Rannells |
| 1,385,346 A | 7/1921 | Taylor |
| 1,709,520 A | 4/1929 | Chandler |

(Continued)

FOREIGN PATENT DOCUMENTS

| AU | 550575 | 5/1983 |
|---|---|---|

(Continued)

OTHER PUBLICATIONS

Davydov, et al. Vesten. Khir., Sep. 1088—"Vacuum Therapy in the Treatment of Acture Suppurative Diseases of Soft Tissues and Suppurative Wounds" (English translation by R. McElroy Translation Co., Austin, Texas).

(Continued)

*Primary Examiner* — Patricia M Bianco
*Assistant Examiner* — Brandon Jackson

(57) ABSTRACT

A wound care bandage for treating a wound is provided. The bandage includes an SIS layer to be placed on the wound surface and a cover to placed over the wound. Illustratively, the bandage further includes a structure to provide a vacuum space. A method for promoting wound healing is further provided. The method includes applying the above-mentioned wound care bandage to the wound and creating a vacuum in the vacuum space to draw blood controllably from the wound into the SIS layer.

10 Claims, 2 Drawing Sheets

U.S. PATENT DOCUMENTS

| | | | |
|---|---|---|---|
| 1,936,129 A | 11/1933 | Fisk | |
| 2,078,180 A | 4/1937 | Kronenberg | 128/276 |
| 2,195,771 A | 4/1940 | Estler | |
| 2,221,758 A | 11/1940 | Elmquist | |
| 2,305,289 A | 12/1942 | Coburg | 128/132 |
| 2,338,339 A | 1/1944 | LaMere et al. | |
| 2,443,481 A | 6/1948 | Sene | |
| 2,547,758 A | 4/1951 | Keeling | |
| 2,560,915 A | 7/1951 | Bamberger | 128/350 |
| 2,573,791 A | 11/1951 | Howells | |
| 2,577,945 A | 12/1951 | Atherton | |
| 2,632,443 A | 3/1953 | Lesher | |
| 2,682,873 A | 6/1954 | Evans et al. | |
| 2,910,763 A | 11/1959 | Lauterbach | 128/72.2 |
| 2,969,057 A | 1/1961 | Simmons | |
| 3,026,874 A | 3/1962 | Stevens | |
| 3,066,672 A | 12/1962 | Crosby, Jr. et al. | 128/276 |
| 3,315,665 A | 4/1967 | MacLeod | |
| 3,367,332 A | 2/1968 | Groves | |
| 3,382,867 A | 5/1968 | Reaves | |
| 3,430,631 A | 3/1969 | Abramson | 128/350 |
| 3,492,991 A | 2/1970 | Dyer, Jr. | 128/214 |
| 3,520,300 A | 7/1970 | Flower, Jr. | |
| 3,528,416 A | 9/1970 | Chamberlain | |
| 3,568,675 A | 3/1971 | Harvey | |
| 3,585,742 A | 6/1971 | Tyler | 40/10 |
| 3,599,639 A | 8/1971 | Spotz | |
| 3,610,238 A | 10/1971 | Rich, Jr. | |
| 3,623,087 A | 11/1971 | Gallichotte | 340/412 |
| 3,626,087 A | 12/1971 | Tomioka | 178/5.4 |
| 3,648,692 A | 3/1972 | Wheeler | |
| 3,682,180 A | 8/1972 | McFarlane | |
| 3,683,894 A | 8/1972 | Villari | 128/2 |
| 3,721,244 A | 3/1973 | Elmaleh | 128/304 |
| 3,752,158 A | 8/1973 | Kariher | 128/278 |
| 3,753,439 A | 8/1973 | Brugarolas et al. | 128/350 |
| 3,782,377 A | 1/1974 | Rychlik | |
| 3,812,972 A | 5/1974 | Rosenblum | |
| 3,814,095 A | 6/1974 | Lubens | |
| 3,823,720 A | 7/1974 | Tribble | 128/350 |
| 3,826,254 A | 7/1974 | Mellor | |
| 3,831,588 A | 8/1974 | Rindner | |
| 3,860,008 A | 1/1975 | Miner et al. | 128/350 |
| 3,874,387 A | 4/1975 | Barbieri | |
| 3,903,882 A | 9/1975 | Augurt | |
| 3,924,624 A | 12/1975 | Schachet | 128/276 |
| 3,935,863 A | 2/1976 | Kliger | |
| 3,954,105 A | 5/1976 | Nordby et al. | |
| 3,982,546 A | 9/1976 | Friend | 128/350 |
| 4,004,590 A | 1/1977 | Muriot | 128/276 |
| 4,013,076 A | 3/1977 | Puderbaugh et al. | 128/276 |
| RE29,319 E | 7/1977 | Nordby et al. | 128/275 |
| RE29,321 E | 7/1977 | Holbrook | 215/309 |
| 4,058,123 A | 11/1977 | May | 128/278 |
| 4,080,970 A | 3/1978 | Miller | |
| 4,096,853 A | 6/1978 | Weigand | |
| 4,112,947 A | 9/1978 | Nehring | |
| 4,149,541 A | 4/1979 | Gammons et al. | |
| 4,165,748 A | 8/1979 | Johnson | |
| 4,178,974 A | 12/1979 | Levin | |
| 4,184,510 A | 1/1980 | Murry et al. | 137/565 |
| 4,191,204 A | 3/1980 | Nehring | |
| 4,219,021 A | 8/1980 | Fink | 128/214 |
| 4,224,941 A | 9/1980 | Stivala | |
| 4,233,969 A | 11/1980 | Lock et al. | |
| 4,245,630 A | 1/1981 | Lloyd et al. | |
| 4,250,882 A | 2/1981 | Adair | |
| 4,256,109 A | 3/1981 | Nichols | 128/276 |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,341,209 A | 7/1982 | Schaar | |
| 4,364,394 A | 12/1982 | Wilkinson | 604/96 |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,399,816 A | 8/1983 | Spangler | |
| 4,419,097 A | 12/1983 | Rowland | |
| 4,445,897 A | 5/1984 | Ekbladh et al. | 604/280 |
| 4,457,755 A | 7/1984 | Wilson | |
| 4,460,370 A | 7/1984 | Allison et al. | |
| 4,465,062 A | 8/1984 | Versaggi et al. | |
| 4,465,485 A | 8/1984 | Kashmer et al. | 604/320 |
| 4,469,092 A | 9/1984 | Marshall et al. | |
| 4,475,909 A | 10/1984 | Eisenberg | |
| 4,480,638 A | 11/1984 | Schmid | |
| 4,508,533 A | 4/1985 | Abramson | 604/35 |
| 4,525,156 A | 6/1985 | Benusa et al. | 604/28 |
| 4,525,166 A | 6/1985 | Leclerc | |
| 4,525,374 A | 6/1985 | Vaillancourt | |
| 4,533,352 A | 8/1985 | Van Beek et al. | |
| 4,533,419 A | 8/1985 | Pieslak et al. | 156/85 |
| 4,540,412 A | 9/1985 | Van Overloop | |
| 4,543,100 A | 9/1985 | Brodsky | |
| 4,548,202 A | 10/1985 | Duncan | 128/334 |
| 4,551,139 A | 11/1985 | Plaas et al. | |
| 4,553,967 A | 11/1985 | Ferguson et al. | |
| 4,569,348 A | 2/1986 | Hasslinger | |
| 4,569,674 A | 2/1986 | Phillips et al. | |
| 4,573,965 A | 3/1986 | Russo | |
| 4,579,555 A | 4/1986 | Russo | |
| 4,596,564 A | 6/1986 | Spetzler et al. | 604/281 |
| 4,608,041 A | 8/1986 | Nielsen | |
| 4,614,794 A | 9/1986 | Easton et al. | |
| 4,624,656 A | 11/1986 | Clark et al. | |
| 4,633,863 A | 1/1987 | Filips et al. | |
| 4,637,819 A | 1/1987 | Oullette et al. | |
| 4,640,688 A | 2/1987 | Hauser | |
| 4,641,643 A | 2/1987 | Greer | |
| 4,645,492 A | 2/1987 | Weeks | 604/174 |
| 4,655,210 A | 4/1987 | Edenbaum et al. | 128/156 |
| 4,655,754 A | 4/1987 | Richmond et al. | |
| 4,661,093 A | 4/1987 | Beck et al. | |
| 4,664,652 A | 5/1987 | Weilbacher | |
| 4,664,662 A | 5/1987 | Webster | |
| 4,667,666 A | 5/1987 | Frysliie | |
| 4,679,590 A | 7/1987 | Hergenroeder | |
| 4,704,102 A | 11/1987 | Guthery | 604/28 |
| 4,710,165 A | 12/1987 | McNeil et al. | 604/67 |
| 4,713,051 A | 12/1987 | Steppe et al. | 604/30 |
| 4,717,332 A | 1/1988 | Edens | 431/8 |
| 4,717,379 A | 1/1988 | Ekholmer | 604/43 |
| 4,733,659 A | 3/1988 | Edenbaum et al. | |
| 4,735,606 A | 4/1988 | Davison | 604/28 |
| 4,735,610 A | 4/1988 | Akkas et al. | 604/119 |
| 4,737,148 A | 4/1988 | Blake | 604/126 |
| 4,740,202 A | 4/1988 | Stacey et al. | |
| 4,743,232 A | 5/1988 | Kruger | |
| 4,747,166 A | 5/1988 | Kuntz | |
| 4,758,220 A | 7/1988 | Sundblom et al. | 604/65 |
| 4,759,354 A | 7/1988 | Quarfoot | |
| 4,765,316 A | 8/1988 | Marshall | |
| 4,778,446 A | 10/1988 | Jensen | |
| 4,778,456 A | 10/1988 | Lokken | |
| 4,787,888 A | 11/1988 | Fox | |
| 4,798,578 A | 1/1989 | Ranford | 604/4 |
| 4,820,265 A | 4/1989 | DeSatnick et al. | |
| 4,820,284 A | 4/1989 | Hauri | |
| 4,826,494 A | 5/1989 | Richmond et al. | 604/323 |
| 4,826,949 A | 5/1989 | Stanko | |
| 4,834,110 A | 5/1989 | Richard | |
| 4,838,883 A | 6/1989 | Matsuura | |
| 4,840,187 A | 6/1989 | Brazier | |
| 4,841,962 A | 6/1989 | Berg et al. | |
| 4,850,350 A | 7/1989 | Jackson | 128/207.16 |
| 4,863,449 A | 9/1989 | Therriault et al. | |
| 4,872,450 A | 10/1989 | Austad | |
| 4,878,901 A | 11/1989 | Sachse | |
| 4,890,608 A | 1/1990 | Steer | |
| 4,897,081 A | 1/1990 | Poirier et al. | |
| 4,900,302 A | 2/1990 | Newton | 604/30 |
| 4,902,508 A | 2/1990 | Badylak et al. | |
| 4,906,233 A | 3/1990 | Moriuchi et al. | |
| 4,906,240 A | 3/1990 | Reed et al. | |

| Patent No. | Date | Name | | Patent No. | Date | Name |
|---|---|---|---|---|---|---|
| 4,915,694 A | 4/1990 | Yamamoto et al. | | 5,330,452 A | 7/1994 | Zook |
| 4,917,112 A | 4/1990 | Kalt | | 5,335,651 A | 8/1994 | Foster et al. ............. 128/202.13 |
| 4,919,654 A | 4/1990 | Kalt | | 5,338,293 A | 8/1994 | Jeppsson et al. ................ 604/29 |
| 4,921,492 A | 5/1990 | Schultz et al. | | 5,342,293 A | 8/1994 | Zanger ............................ 604/22 |
| 4,930,997 A | 6/1990 | Bennett | | 5,342,301 A | 8/1994 | Saab ................................ 604/96 |
| 4,941,882 A | 7/1990 | Ward et al. | | 5,342,376 A | 8/1994 | Ruff .............................. 606/151 |
| 4,950,230 A | 8/1990 | Kendell ........................ 604/28 | | 5,344,415 A | 9/1994 | DeBusk et al. |
| 4,953,565 A | 9/1990 | Tachibana et al. | | 5,349,965 A | 9/1994 | McCarver |
| 4,956,178 A | 9/1990 | Badylak et al. | | 5,352,463 A | 10/1994 | Badylak et al. |
| 4,957,492 A | 9/1990 | McVay ......................... 604/319 | | 5,358,494 A | 10/1994 | Svedman |
| 4,969,880 A | 11/1990 | Zamierowski | | 5,370,610 A | 12/1994 | Reynolds ......................... 604/43 |
| 4,969,881 A | 11/1990 | Viesturs | | 5,372,821 A | 12/1994 | Badylak et al. |
| 4,970,298 A | 11/1990 | Silver et al. | | 5,374,254 A | 12/1994 | Buma |
| 4,985,019 A | 1/1991 | Michelson | | 5,376,252 A | 12/1994 | Ekstrom et al. |
| 4,988,336 A | 1/1991 | Kohn | | 5,380,280 A | 1/1995 | Peterson |
| 4,990,144 A | 2/1991 | Blott | | 5,395,315 A | 3/1995 | Griep |
| 4,991,574 A | 2/1991 | Pocknell | | 5,409,013 A | 4/1995 | Clement ........................ 128/753 |
| 4,994,022 A | 2/1991 | Steffler et al. ...................... 604/7 | | 5,413,788 A | 5/1995 | Edwards et al. .............. 424/409 |
| 4,997,425 A | 3/1991 | Shioya et al. | | 5,419,768 A | 5/1995 | Kayser |
| 5,000,172 A | 3/1991 | Ward ............................ 128/155 | | 5,431,622 A | 7/1995 | Pyrozyk et al. |
| 5,000,741 A | 3/1991 | Kalt .............................. 604/180 | | 5,437,622 A | 8/1995 | Carion ............................ 602/57 |
| 5,002,528 A | 3/1991 | Palestrant | | 5,437,651 A | 8/1995 | Todd et al. |
| 5,002,529 A | 3/1991 | Cunningham | | 5,439,452 A | 8/1995 | McCarty ....................... 604/248 |
| 5,003,971 A | 4/1991 | Buckley | | 5,445,604 A | 8/1995 | Lang |
| 5,034,003 A | 7/1991 | Denance | | 5,445,833 A | 8/1995 | Badylak et al. |
| 5,034,006 A | 7/1991 | Hosoda et al. | | 5,447,505 A | 9/1995 | Valentine et al. ............. 604/304 |
| 5,035,865 A | 7/1991 | Inaba et al. ...................... 422/99 | | 5,449,383 A | 9/1995 | Chatelier et al. |
| 5,037,397 A | 8/1991 | Kalt et al. | | 5,451,215 A | 9/1995 | Wolter |
| 5,042,978 A | 8/1991 | Quenin et al. | | 5,451,373 A | 9/1995 | Lewis et al. ................. 422/82.13 |
| 5,045,777 A | 9/1991 | Itagaki | | 5,478,333 A | 12/1995 | Asherman, Jr. |
| 5,060,662 A | 10/1991 | Farnswoth, III | | 5,484,420 A | 1/1996 | Russo |
| 5,071,409 A | 12/1991 | Rosenberg .................... 604/119 | | 5,484,427 A | 1/1996 | Gibbons |
| 5,073,172 A | 12/1991 | Fell | | 5,484,428 A | 1/1996 | Drainville et al. |
| 5,080,650 A | 1/1992 | Hirsch et al. .................. 604/104 | | 5,487,889 A | 1/1996 | Eckert et al. |
| 5,086,170 A | 2/1992 | Luheshi et al. ............... 540/303 | | 5,516,533 A | 5/1996 | Badylak et al. |
| 5,086,763 A | 2/1992 | Hathman | | 5,520,652 A | 5/1996 | Peterson |
| 5,086,764 A | 2/1992 | Gilman | | 5,527,293 A | 6/1996 | Zamierowski |
| 5,092,858 A | 3/1992 | Benson et al. ................ 604/319 | | 5,531,670 A | 7/1996 | Westby et al. |
| 5,100,395 A | 3/1992 | Rosenberg .................... 604/284 | | 5,533,981 A | 7/1996 | Mandro et al. |
| 5,100,396 A | 3/1992 | Zamierowski | | 5,534,346 A | 7/1996 | Robinson ....................... 428/343 |
| 5,101,808 A | 4/1992 | Kobayashi et al. | | 5,540,668 A | 7/1996 | Wilson et al. ................. 604/248 |
| 5,106,362 A | 4/1992 | Gilman | | 5,542,918 A | 8/1996 | Atkinson |
| 5,106,629 A | 4/1992 | Cartmell et al. | | 5,554,389 A | 9/1996 | Badylak et al. |
| 5,108,364 A | 4/1992 | Takezawa et al. .............. 604/43 | | 5,556,375 A | 9/1996 | Ewall |
| 5,134,994 A | 8/1992 | Say ........................... 128/200.24 | | 5,558,639 A | 9/1996 | Gangemi et al. ................ 604/67 |
| 5,135,518 A | 8/1992 | Vera | | 5,573,784 A | 11/1996 | Badylak et al. |
| 5,146,925 A | 9/1992 | Snow ............................ 128/658 | | 5,578,022 A | 11/1996 | Scherson et al. |
| 5,147,338 A | 9/1992 | Lang et al. | | 5,578,662 A | 11/1996 | Bennett et al. |
| 5,149,331 A | 9/1992 | Ferdman et al. | | 5,607,388 A | 3/1997 | Ewall |
| 5,152,757 A | 10/1992 | Eriksson | | 5,621,035 A | 4/1997 | Lyles et al. |
| 5,160,322 A | 11/1992 | Scheremet et al. | | 5,624,418 A | 4/1997 | Shepard |
| 5,167,613 A | 12/1992 | Karami et al. | | 5,628,735 A | 5/1997 | Skow |
| 5,167,622 A | 12/1992 | Muto .............................. 604/35 | | 5,629,186 A | 5/1997 | Yasukawa et al. |
| 5,170,781 A | 12/1992 | Loomis | | 5,631,011 A | 5/1997 | Wadstrom |
| 5,176,502 A | 1/1993 | Sanderson et al. | | 5,635,201 A | 6/1997 | Fabo ............................. 424/443 |
| 5,176,663 A | 1/1993 | Svedman et al. | | 5,636,643 A | 6/1997 | Argenta et al. |
| 5,181,908 A | 1/1993 | Bell ................................ 604/24 | | 5,641,518 A | 6/1997 | Badylak et al. |
| 5,189,609 A | 2/1993 | Tivig et al. ................. 364/413.01 | | 5,645,081 A | 7/1997 | Argenta et al. |
| 5,197,948 A | 3/1993 | Ghodsian ........................ 604/30 | | 5,645,860 A | 7/1997 | Knapp et al. |
| 5,215,522 A | 6/1993 | Page et al. ....................... 604/33 | | 5,655,258 A | 8/1997 | Heintz |
| 5,215,539 A | 6/1993 | Schoolman | | 5,656,027 A | 8/1997 | Ellingboe |
| 5,224,929 A | 7/1993 | Remiszewski .................. 604/30 | | 5,662,598 A | 9/1997 | Tobin |
| 5,228,431 A | 7/1993 | Giarretto | | 5,662,624 A | 9/1997 | Sundstrom et al. |
| 5,230,350 A | 7/1993 | Fentress | | 5,662,625 A | 9/1997 | Westwood |
| 5,232,453 A | 8/1993 | Plass et al. | | 5,669,892 A | 9/1997 | Keogh et al. |
| 5,238,654 A | 8/1993 | Nohl et al. | | 5,672,151 A | 9/1997 | Calderon-Garciduenas ... 602/21 |
| 5,249,121 A | 9/1993 | Baum et al. ................ 364/413.01 | | 5,674,193 A | 10/1997 | Hayes ............................. 604/28 |
| 5,256,418 A | 10/1993 | Kemp et al. | | 5,678,564 A | 10/1997 | Lawrence et al. |
| 5,261,893 A | 11/1993 | Zamierowski | | 5,681,290 A | 10/1997 | Alexander ..................... 604/180 |
| 5,263,922 A | 11/1993 | Sova et al. | | 5,690,815 A | 11/1997 | Krasnoff et al. |
| 5,265,605 A | 11/1993 | Afflerbach .................... 128/630 | | 5,695,998 A | 12/1997 | Badylak et al. |
| 5,275,826 A | 1/1994 | Badylak et al. | | 5,697,920 A | 12/1997 | Gibbons |
| 5,278,100 A | 1/1994 | Doan et al. .................... 437/200 | | 5,711,969 A | 1/1998 | Patel et al. |
| 5,279,550 A | 1/1994 | Habib et al. ..................... 604/38 | | 5,718,955 A | 2/1998 | McGuire ....................... 428/35.7 |
| 5,281,422 A | 1/1994 | Badylak et al. | | 5,735,833 A | 4/1998 | Olson |
| 5,291,887 A | 3/1994 | Stanley et al. | | 5,738,656 A | 4/1998 | Wagner ......................... 604/119 |
| 5,298,015 A | 3/1994 | Komatsuzaki et al. | | 5,741,237 A | 4/1998 | Walker |
| 5,306,298 A | 4/1994 | Godley, III ....................... 623/9 | | 5,749,842 A | 5/1998 | Cheong et al. .................. 602/41 |
| 5,314,409 A | 5/1994 | Sarosiek et al. ................ 604/101 | | 5,753,267 A | 5/1998 | Badylak et al. |

| Patent No. | Date | Name | Class |
|---|---|---|---|
| 5,755,791 A | 5/1998 | Whitson et al. | |
| 5,759,570 A | 6/1998 | Arnold | |
| 5,762,640 A | 6/1998 | Kajiwara et al. | |
| 5,762,966 A | 6/1998 | Knapp et al. | |
| 5,780,281 A | 7/1998 | Yasukawa et al. | |
| 5,782,871 A | 7/1998 | Fujiwara et al. | |
| 5,795,584 A | 8/1998 | Totakura et al. | |
| 5,800,383 A | 9/1998 | Chandler et al. | 604/35 |
| 5,817,145 A | 10/1998 | Augustine et al. | |
| 5,827,246 A | 10/1998 | Bowen | |
| 5,827,296 A | 10/1998 | Morris et al. | 606/129 |
| 5,855,619 A | 1/1999 | Caplan et al. | |
| 5,866,414 A | 2/1999 | Badylak et al. | |
| 5,881,723 A | 3/1999 | Wallace et al. | 128/204.21 |
| 5,891,111 A | 4/1999 | Ismael | 604/280 |
| 5,902,874 A | 5/1999 | Roby et al. | |
| 5,902,875 A | 5/1999 | Roby et al. | |
| 5,911,222 A | 6/1999 | Lawrence et al. | |
| 5,914,387 A | 6/1999 | Roby et al. | |
| 5,919,476 A | 7/1999 | Fischer et al. | |
| 5,921,972 A | 7/1999 | Skow | |
| 5,928,174 A | 7/1999 | Gibbins | |
| 5,931,304 A | 8/1999 | Hammond | 206/570 |
| 5,941,859 A | 8/1999 | Lerman | |
| 5,942,496 A | 8/1999 | Bonadio et al. | |
| 5,947,914 A | 9/1999 | Augustine | |
| 5,951,295 A | 9/1999 | Lyles et al. | |
| 5,954,680 A | 9/1999 | Augustine | |
| 5,961,480 A | 10/1999 | Augustine | |
| 5,962,427 A | 10/1999 | Goldstein et al. | |
| 5,964,721 A | 10/1999 | Augustine | |
| 5,964,723 A | 10/1999 | Augustine | |
| 5,986,163 A | 11/1999 | Augustine | |
| 5,997,568 A | 12/1999 | Liu | |
| 6,010,527 A | 1/2000 | Augustine et al. | |
| 6,013,048 A | 1/2000 | Podany et al. | 604/22 |
| 6,017,493 A | 1/2000 | Cambron et al. | |
| 6,039,724 A | 3/2000 | Seifert et al. | |
| 6,045,518 A | 4/2000 | Augustine | |
| 6,045,541 A | 4/2000 | Matsumoto et al. | |
| 6,051,747 A | 4/2000 | Lindqvist et al. | 602/46 |
| 6,056,730 A | 5/2000 | Greter | |
| 6,071,254 A | 6/2000 | Augustine | |
| 6,071,267 A | 6/2000 | Zamierowski | |
| 6,071,304 A | 6/2000 | Augustine et al. | |
| 6,080,189 A | 6/2000 | Augustine et al. | |
| 6,080,243 A | 6/2000 | Insley et al. | |
| 6,093,160 A | 7/2000 | Augustine et al. | |
| 6,093,230 A | 7/2000 | Johnson, III et al. | |
| 6,095,992 A | 8/2000 | Augustine | |
| 6,099,567 A | 8/2000 | Badylak et al. | |
| 6,110,197 A | 8/2000 | Augustine et al. | |
| 6,113,561 A | 9/2000 | Augustine | |
| 6,117,111 A | 9/2000 | Fleischmann | |
| 6,135,116 A | 10/2000 | Vogel et al. | |
| 6,142,982 A | 11/2000 | Hunt et al. | |
| 6,143,945 A | 11/2000 | Augustine et al. | |
| 6,149,614 A | 11/2000 | Dunshee et al. | 602/57 |
| 6,171,344 B1 | 1/2001 | Atala | |
| 6,174,306 B1 | 1/2001 | Fleischmann | |
| 6,203,563 B1 | 3/2001 | Fernandez | |
| 6,206,931 B1 | 3/2001 | Cook et al. | |
| 6,207,875 B1 | 3/2001 | Lindqvist et al. | |
| 6,213,965 B1 | 4/2001 | Augustine et al. | |
| 6,213,966 B1 | 4/2001 | Augustine | |
| 6,217,535 B1 | 4/2001 | Augustine | |
| 6,235,009 B1 | 5/2001 | Skow | |
| 6,235,047 B1 | 5/2001 | Augustine et al. | |
| 6,241,697 B1 | 6/2001 | Augustine | |
| 6,241,698 B1 | 6/2001 | Augustine | |
| 6,241,747 B1 | 6/2001 | Ruff | 606/216 |
| 6,244,311 B1 | 6/2001 | Hand et al. | |
| 6,248,084 B1 | 6/2001 | Augustine et al. | |
| 6,254,557 B1 | 7/2001 | Augustine et al. | |
| 6,254,580 B1 | 7/2001 | Svedman | |
| 6,259,067 B1 | 7/2001 | Faries, Jr. et al. | 219/428 |
| 6,264,622 B1 | 7/2001 | Augustine | |
| 6,264,979 B1 | 7/2001 | Svedman | |
| 6,267,740 B1 | 7/2001 | Augustine et al. | |
| 6,283,931 B1 | 9/2001 | Augustine | |
| 6,284,941 B1 | 9/2001 | Cox et al. | |
| 6,287,316 B1 | 9/2001 | Agarwal et al. | 606/151 |
| 6,290,685 B1 | 9/2001 | Insley et al. | |
| 6,293,917 B1 | 9/2001 | Augustine et al. | |
| 6,325,798 B1 | 12/2001 | Edwards et al. | 606/41 |
| 6,345,623 B1 | 2/2002 | Heaton et al. | |
| 6,364,853 B1 | 4/2002 | French et al. | 604/35 |
| 6,394,142 B1 | 5/2002 | Woelfel et al. | 138/115 |
| 6,398,767 B1 | 6/2002 | Fleischmann | |
| 6,410,427 B1 | 6/2002 | Hu | 438/655 |
| 6,440,427 B1 | 8/2002 | Wadstrom | |
| 6,458,109 B1 | 10/2002 | Henley et al. | |
| 6,471,685 B1 | 10/2002 | Johnson | 604/890.1 |
| 6,472,581 B1 | 10/2002 | Muramatsu | 602/41 |
| 6,488,643 B1 | 12/2002 | Tumey et al. | |
| 6,491,682 B2 | 12/2002 | Paderni | |
| 6,491,693 B1 | 12/2002 | Lytinas | 606/53 |
| 6,493,568 B1 | 12/2002 | Bell et al. | |
| 6,500,112 B1 | 12/2002 | Khouri | 600/38 |
| 6,520,982 B1 | 2/2003 | Boynton et al. | 607/104 |
| 6,553,998 B2 | 4/2003 | Heaton et al. | 128/897 |
| 6,557,704 B1 | 5/2003 | Randolph | 206/363 |
| 6,559,773 B1 | 5/2003 | Berry | 340/815.4 |
| 6,599,277 B2 | 7/2003 | Neubert | 604/317 |
| 6,626,891 B2 | 9/2003 | Ohmstede | 604/543 |
| 6,638,270 B2 | 10/2003 | Johnson | 604/890.1 |
| 6,648,862 B2 | 11/2003 | Watson | |
| 6,663,349 B1 | 12/2003 | Discenzo et al. | |
| 6,685,681 B2 | 2/2004 | Lockwood et al. | |
| 6,691,047 B1 | 2/2004 | Fredericks | |
| 6,695,823 B1 | 2/2004 | Lina et al. | |
| 6,695,824 B2 | 2/2004 | Howard et al. | 604/305 |
| 6,719,779 B2 | 4/2004 | Daoud | 607/105 |
| 6,749,592 B2 | 6/2004 | Lord | |
| 6,752,794 B2 | 6/2004 | Lockwood et al. | 604/313 |
| 6,755,807 B2 | 6/2004 | Risk, Jr. et al. | 604/319 |
| 6,764,462 B2 | 7/2004 | Risk, Jr. et al. | 604/67 |
| 6,767,334 B1 | 7/2004 | Randolph | 604/35 |
| 6,800,074 B2 | 10/2004 | Henley et al. | 604/319 |
| 6,814,079 B2 | 11/2004 | Heaton et al. | 128/897 |
| 6,824,533 B2 | 11/2004 | Risk, Jr. et al. | 604/319 |
| 6,855,135 B2 | 2/2005 | Lockwood et al. | 604/313 |
| 6,856,821 B2 | 2/2005 | Johnson | 600/345 |
| 6,936,037 B2 | 8/2005 | Bubb et al. | 604/327 |
| 6,951,553 B2 | 10/2005 | Bubb et al. | 604/327 |
| 6,966,889 B2 | 11/2005 | Saab | 604/96.01 |
| 6,979,324 B2 | 12/2005 | Bybordi et al. | 604/313 |
| 6,994,702 B1 | 2/2006 | Johnson | 606/9 |
| 7,004,915 B2 | 2/2006 | Boynton et al. | 601/6 |
| 7,022,113 B2 | 4/2006 | Lockwood et al. | 604/313 |
| 7,070,584 B2 | 7/2006 | Johnson et al. | |
| 7,077,832 B2 * | 7/2006 | Fleischmann | 604/304 |
| 7,108,683 B2 | 9/2006 | Zamierowski | 604/304 |
| 7,117,869 B2 | 10/2006 | Heaton et al. | 128/897 |
| 7,128,735 B2 | 10/2006 | Weston | 604/543 |
| 7,144,390 B1 | 12/2006 | Hannigan et al. | 604/313 |
| 7,195,624 B2 | 3/2007 | Lockwood et al. | 604/543 |
| 7,245,291 B2 | 7/2007 | Sharif et al. | 345/172 |
| 7,276,051 B1 | 10/2007 | Henley et al. | 604/304 |
| 7,338,482 B2 | 3/2008 | Lockwood et al. | 604/543 |
| 7,381,211 B2 | 6/2008 | Zamierowski | 606/215 |
| 7,422,576 B2 | 9/2008 | Boynton et al. | 607/104 |
| 7,524,286 B2 | 4/2009 | Johnson | 600/309 |
| 7,534,927 B2 | 5/2009 | Lockwood et al. | 602/46 |
| 2001/0029956 A1 | 10/2001 | Argenta et al. | |
| 2001/0034494 A1 | 10/2001 | Sessions et al. | 602/46 |
| 2001/0043943 A1 | 11/2001 | Coffey | 424/447 |
| 2001/0052681 A1 | 12/2001 | Deavila | 280/47.19 |
| 2002/0065494 A1 | 5/2002 | Lockwood et al. | |
| 2002/0077661 A1 | 6/2002 | Saadat | 606/221 |
| 2002/0082567 A1 | 6/2002 | Lockwood et al. | 604/313 |
| 2002/0082668 A1 | 6/2002 | Ingman | |
| 2002/0085952 A1 | 7/2002 | Ellingboe et al. | 422/45 |
| 2002/0115951 A1 | 8/2002 | Norstrem et al. | |
| 2002/0115952 A1 | 8/2002 | Johnson et al. | |
| 2002/0120185 A1 | 8/2002 | Johnson | |
| 2002/0143286 A1 | 10/2002 | Tumey | |
| 2002/0161317 A1 | 10/2002 | Risk et al. | |

| | | | | | |
|---|---|---|---|---|---|
| 2002/0183702 A1 | 12/2002 | Henley et al. .............. 604/305 | EP | 0 880 953 A2 | 12/1998 |
| 2002/0193723 A1 | 12/2002 | Batdorf et al. ............... 602/48 | EP | 1 088 569 A2 | 4/2001 |
| 2003/0032951 A1 | 2/2003 | Rittman, III et al. .......... 606/34 | EP | 1 100 574 | 5/2001 |
| 2003/0077311 A1 | 4/2003 | Vyakarnam et al. | EP | 1 190 732 A1 | 3/2002 |
| 2003/0093041 A1 | 5/2003 | Risk, Jr. et al. .............. 604/305 | EP | 1 018 967 B1 | 8/2004 |
| 2003/0143352 A1 | 7/2003 | Yang et al. .................. 428/36.9 | EP | 1 726 276 | 11/2006 |
| 2003/0219469 A1 | 11/2003 | Johnson et al. .............. 604/500 | FR | 500253 | 3/1920 |
| 2003/0225441 A1 | 12/2003 | Boynton et al. .............. 607/104 | FR | 1303238 | 7/1962 |
| 2004/0039415 A1 | 2/2004 | Zamierowski ................ 606/215 | GB | 3090 | 6/1902 |
| 2004/0064111 A1 | 4/2004 | Lockwood et al. ........... 604/305 | GB | 641061 | 8/1950 |
| 2004/0167482 A1 | 8/2004 | Watson ........................ 604/317 | GB | 692578 | 6/1953 |
| 2004/0225208 A1 | 11/2004 | Johnson ....................... 600/364 | GB | 1549756 | 8/1979 |
| 2004/0243073 A1 | 12/2004 | Lockwood et al. ........... 604/313 | GB | 1584772 | 2/1981 |
| 2004/0249353 A1 | 12/2004 | Risk, Jr. et al. .............. 604/315 | GB | 2195255 A | 4/1988 |
| 2004/0260230 A1 | 12/2004 | Randolph ..................... 604/28 | GB | 2197789 A | 6/1988 |
| 2005/0004534 A1 | 1/2005 | Lockwood et al. ........... 604/304 | GB | 2220357 A | 1/1990 |
| 2005/0010153 A1 | 1/2005 | Lockwood et al. ........... 602/41 | GB | 2235877 A | 3/1991 |
| 2005/0033197 A1 | 2/2005 | Cottler ......................... 600/573 | GB | 2307180 | 5/1997 |
| 2005/0065484 A1 | 3/2005 | Watson, Jr. ................... 604/289 | GB | 2329127 A | 3/1999 |
| 2005/0070858 A1 | 3/2005 | Lockwood et al. ........... 604/319 | GB | 2333965 A | 8/1999 |
| 2005/0085795 A1 | 4/2005 | Lockwood et al. ........... 604/543 | GB | 2336546 A | 10/1999 |
| 2005/0090787 A1 | 4/2005 | Risk, Jr. et al. .............. 604/305 | GB | 2342584 A | 4/2000 |
| 2005/0131327 A1 | 6/2005 | Lockwood et al. ........... 602/41 | GB | 2344531 A | 6/2000 |
| 2005/0177190 A1 | 8/2005 | Zamierowski ................ 606/215 | GB | 2351025 A | 12/2000 |
| 2005/0182445 A1 | 8/2005 | Zamierowski ................ 606/215 | GB | 2356148 | 5/2001 |
| 2005/0182446 A1 | 8/2005 | DeSantis ...................... 606/222 | HU | 199304 B | 1/1989 |
| 2005/0234485 A1 | 10/2005 | Seegert et al. ............... 606/131 | HU | 51150 | 4/1990 |
| 2005/0234510 A1 | 10/2005 | Zamierowski ................ 606/215 | HU | 205557 B | 4/1990 |
| 2005/0240220 A1 | 10/2005 | Zamierowski ................ 606/215 | HU | P9006526 | 1/1993 |
| 2005/0283105 A1 | 12/2005 | Heaton et al. ................ 128/897 | HU | P9302966 | 7/1996 |
| 2006/0015087 A1 | 1/2006 | Risk, Jr. et al. .............. 604/541 | HU | 76351 | 8/1997 |
| 2006/0029650 A1 | 2/2006 | Coffey ......................... 424/443 | HU | 215563 B | 8/1997 |
| 2006/0029675 A1 | 2/2006 | Ginther ........................ 424/400 | HU | 1666 | 12/1999 |
| 2006/0041247 A1 | 2/2006 | Petrosenko et al. .......... 604/247 | JP | 57-177758 | 11/1982 |
| 2006/0079852 A1 | 4/2006 | Bubb et al. ................... 604/289 | JP | 4-129436 | 4/1992 |
| 2006/0129137 A1 | 6/2006 | Lockwood et al. ........... 604/543 | JP | 6-327761 | 11/1994 |
| 2006/0149170 A1 | 7/2006 | Boynton et al. .............. 601/6 | SE | 84485 | 10/1935 |
| 2006/0149171 A1 | 7/2006 | Vogel et al. .................. 601/11 | SG | 71559 | 4/2002 |
| 2006/0173253 A1 | 8/2006 | Ganapathy et al. .......... 600/364 | SU | 587941 | 1/1978 |
| 2006/0189910 A1 | 8/2006 | Johnson et al. .............. 602/43 | SU | 1268175 A1 | 11/1986 |
| 2006/0213527 A1 | 9/2006 | Argenta et al. ............... 128/897 | WO | WO 80/02182 | 10/1980 |
| 2007/0005028 A1 | 1/2007 | Risk, Jr. et al. .............. 604/315 | WO | WO 87/04626 | 8/1987 |
| 2007/0014837 A1 | 1/2007 | Johnson et al. .............. 424/443 | WO | WO 89/04158 | 5/1989 |
| 2007/0021697 A1 | 1/2007 | Ginther et al. ............... 602/1 | WO | WO 90/10424 | 9/1990 |
| 2007/0021698 A1 | 1/2007 | Fleischmann ................ 602/2 | WO | WO 90/11795 | 10/1990 |
| 2007/0032778 A1 | 2/2007 | Heaton et al. ................ 604/540 | WO | WO 91/00718 | 1/1991 |
| 2007/0038172 A1 | 2/2007 | Zamierowski ................ 604/20 | WO | WO 91/08793 | 6/1991 |
| 2007/0156104 A1 | 7/2007 | Lockwood et al. ........... 604/305 | WO | WO 91/16030 | 10/1991 |
| 2007/0233022 A1 | 10/2007 | Henley et al. ................ 604/305 | WO | WO 92/12750 | 8/1992 |
| 2009/0082740 A1 | 3/2009 | Lockwood et al. ........... 602/41 | WO | WO92/19313 | 11/1992 |
| 2010/0063483 A1 | 3/2010 | Adahan ........................ 604/543 | WO | WO 92/20299 | 11/1992 |
| | | | WO | WO 93/09715 | 5/1993 |
| FOREIGN PATENT DOCUMENTS | | | WO | WO 93/09727 | 5/1993 |
| AU | 745271 | 4/1999 | WO | WO 94/00090 | 1/1994 |
| AU | 755496 | 2/2002 | WO | WO 94/20041 | 9/1994 |
| CA | 1127488 | 7/1982 | WO | WO 96/05873 | 2/1996 |
| CA | 2005436 | 6/1990 | WO | WO 96/15745 | 5/1996 |
| CA | 2303085 | 3/1999 | WO | WO97/18007 | 5/1997 |
| DE | 372727 | 3/1923 | WO | WO 98/02205 | 1/1998 |
| DE | 2640413 A1 | 3/1978 | WO | WO 98/38944 | 9/1998 |
| DE | 28 09 828 A1 | 9/1978 | WO | WO 99/01173 | 1/1999 |
| DE | 3102674 A1 | 9/1982 | WO | WO 99/13793 | 3/1999 |
| DE | 3539533 A1 | 5/1987 | WO | WO 99/23990 | 5/1999 |
| DE | 4012232 A * | 10/1991 | WO | WO 99/59816 | 11/1999 |
| DE | 4111122 A1 | 4/1993 | WO | WO 00/07653 | 2/2000 |
| DE | 4306478 A1 | 9/1994 | WO | WO 00/15277 | 3/2000 |
| DE | 29504378 U1 | 10/1995 | WO | WO 00/21586 | 4/2000 |
| DE | 29715634 | 11/1997 | WO | WO 00/26100 | 5/2000 |
| DE | 19722075 C1 | 10/1998 | WO | WO 00/28890 | 5/2000 |
| DK | 64055 | 10/1945 | WO | WO 00/30567 | 6/2000 |
| EP | 0 100 148 | 2/1984 | WO | WO 00/32247 | 6/2000 |
| EP | 0117632 A2 | 9/1984 | WO | WO 00/38552 | 7/2000 |
| EP | 0 161 865 A2 | 11/1985 | WO | WO 00/38755 | 7/2000 |
| EP | 0 358 302 A2 | 3/1990 | WO | WO 00/42958 | 7/2000 |
| EP | 0424165 A1 | 4/1991 | WO | WO 00/59418 | 10/2000 |
| EP | 0485657 A1 | 5/1992 | WO | WO 00/59424 | 10/2000 |
| EP | 0547496 A1 | 6/1993 | WO | WO 00/61206 | 10/2000 |
| EP | 0853 950 A1 | 7/1998 | WO | WO 00/64394 | 11/2000 |
| EP | 0 777 504 B1 | 10/1998 | WO | WO 01/34223 A1 | 5/2001 |

| | | | |
|---|---|---|---|
| WO | WO 01/37922 A2 | 5/2001 | |
| WO | WO 01/49233 A1 | 7/2001 | |
| WO | WO 01/85248 A1 | 11/2001 | |
| WO | WO 01/89431 | 11/2001 | |
| WO | WO 02/38091 | 5/2002 | |
| WO | WO 02/43634 | 6/2002 | |
| WO | WO 03/005943 | 1/2003 | |
| WO | WO 03/045492 | 6/2003 | |
| WO | WO 03/057071 | 7/2003 | |
| WO | WO 03/057307 | 7/2003 | |
| WO | WO 03/101508 | 12/2003 | |

OTHER PUBLICATIONS

Brochure—Augustine Medical, Warm-Up Active Wound Therapy Wound Covers, 1999; 3 pages.
Brochure—Series 55—Emerson Post-Operative Suction Pumps; 1 page.
Brochure—Emerson Transport Suction Unit; 1 page.
Davydov, et al., Vestn. Khir. Mar. 1990—"Basis of the Use of Forced Early Secondary Suture in the Treament of Suppurative Wound by the Vacuum Therapy Method" (English translation by R. McElroy Translation Co., Austin, Texas).
Mirazimov, et al. Ortop Travmatol Protez. Oct. 1966—"Free Skin Graft of the Foot with Preparation of the Wound Surface by Vacuum Treatment" (English translation by R. McElroy Translation Co., Austin, Texas).
Borzov, et al., Vestn. Dermatol. Venerol., Aug. 1965—"Vacuum Therapy of Some Skin Diseases" (English translation by R. McElroy Translation Co., Austin, Texas).
Jeter, et al., Chronic Wound Care: 27: pp. 240-246—"Managing Draining Wounds and Fistulae: New and Established Methods".
Mulder, et al., Wound Healing Publications 1991—"Clinicians' Pocket Guide to Chronic Wound Repair".
Valenta, AIN Apr. 1994; pp. 44-45—"Using the Vacuum Dressing Alternative for Difficult Wounds".
Wolthuis, et al., Physiological Reviews Jul. 1974; vol. 54, No. 3, pp. 566-595—"Physiological Effects of Locally Applied Reduced Pressure in Man".
Fleischmann, WundForum Spezial IHW 1994; pp. 54-55—"Vacuum Sealing for Treatment of Problematical Wounds" (English translation provided).
Bucalo, et al., Wound Repair and Regeneration; Jul.-Sep. 1993; pp. 181-186—"Inhibition of Cell Proliferation by Chronic Wound Fluid".
Olenius, et al., Plastic and Reconstructive Surgery Feb. 1993: pp. 213-215—"Mitotic Activity in Expanded Human Skin".
Viljanto, et al., Br. J. Surg. 1976; vol. 63: pp. 427-430—"Local Hyperalimentation of Open Wounds".
Dunlop, et al., Br. J. Surg. May,1990; vol. 77: pp. 562-563—"Vacuum Drainage of Groin Wounds after Vascular Surgery: A Controlled Trial".
Comment-Ruckley et al., Apr. 1991, pp. 505-506 on "Vacuum Drainage of Groin Wounds after Vascular Surgery".
Landis, et al., Alternate Suction and Pressure, pp. 925-961—"The Effects of Alternative Suction and Pressure on Blood Flow to the Lower Extremities".
Morykwas, et al., Extracellular Matrix and Healing 1993; pp. 800—"Use of Negative Pressure to Increase the Rate of Granulation Tissue Formation in Chronic Open Wounds".
Svedman, et al., Annals of Plastic Surgery Aug. 1986; vol. 17, No. 2: pp. 125-133—"A Dressing System Providing Fluid Supply and Suction Drainage Used for Continuous or Intermittent Irrigation".
Schneider, et al., Plastic and Reconstructive Surgery Sep. 1998, pp. 1195-1198—"A New and Reliable Method of Securing Skin Grafts to the Difficult Recipient Bed".
Morykwas, et al., www.sma.org/soa/jsoawt97—"Nonsurgical Modalities to Enhance Healing and Care of Soft Tissue Wounds"; Feb. 11, 1999; 16 pages.
Chariker, et al., Contemporary Surgery Jun. 1989; vol. 34: pp. 59-63—"Effective Management of Incisional and Cutaneous Fistulae with Closed Suction Wound Drainage".
Tittel, et al., Eingag und Annahme des Manuskripts Jan. 7, 1987; pp. 104-107—"New Standards in Postoperative Wound Drainage".

Genecov, et al., Annals of Plastic Surgery Mar. 1998; vol. 40, No. 3: pp. 219-225—"A Controlled Subatmospheric Pressure Dressing Increases the Rate of Skin Graft Donor Site Reepithelialization".
Morykwas, et al., Annals of Plastic Surgery Jun. 1997; vol. 38, No. 6: pp. 553-562—"Vacuum-Assisted Closure: A New Method for Wound Control and Treatment: Animal Studies and Basic Foundation".
Argenta, et al., Annals of Plastic Surgery Jun. 1997; vol. 38, No. 6: pp. 563-577—"Vacuum-Assisted Closure: A New Method for Wound Control and Treatment: Clinical Experience".
Patent Application and Drawings—"Method of Treating Tissue Damage and Apparatus for Same", consisting of 28 pages.
Patent Application and Drawings—"The Enhancement of Wound Healing and Flap Survival by a New Negative Pressure Device", Argenta et al., consisting of 30 pages.
Nakayama, et al., Ann Plast Surg. May 1991; vol. 26, No. 5: pp. 499-502—"A New Dressing Method for Free Skin Grafting in Hands".
Medical Industry Week—article "KCI Offers New Treatment for Non-Healing Wounds"; 1 page.
Nakayama, et al., Plast. Reconstr. Surg., Dec. 1990.; vol. 86, No. 6: pp. 1216-1219—"A New Method for the Dressing of Free Skin Grafts".
Sames, Br. Med. J., Nov. 5, 1977; vol. 2, No. 6096: 1123—"Sealing of Wounds with Vacuum Drainage".
Fleishmann, et al., Unfallchirurg 1993; 96:488-492—"Vacuum Sealing for Treatment of Soft Tissue Injury in Open Fractures" (English translation of the Summary provided).
Teder, et al., J. Invest. Surg.1990; vol. 3: pp. 399-407—"Continuous Wound Irrigation in the Pig".
Wood, et al., Br. J. of Surg.1977; vol. 64: pp. 554-557—"Foam Elastomer Dressing in the Management of Open Granulating Wounds: Experience with 250 Patients".
Neumann, et al., J. of Biomed. Materials Research 1981, vol. 15: pp. 9-18—"Gelatin-Based Sprayable Foam as a Skin Substitute".
Kostluchenok et al., Vestn. Khir. Sep. 1986—"Vacuum Treatment in the Surgical Treatment of Suppurative Wounds" (English translation by R. McElroy Translation Co., Austin, Texas).
Lundvall, et al., Acta Physiol. Scand. 1989, vol. 136: pp. 403-409—"Transmission of Externally Applied Negative Pressure to the Underlying Tissue. A Study on the Upper Arm of Man".
Brochure—Aeros—Instavac Aspirator; 1 page.
Brochure—Pleur-evac Adult-Pediatric-Non-Metered Disposable "3-Bottle" Unit, A-4000; 6 pages.
Brochure—Hiblow Air Pump; 1 page.
Brochure—Aeros—Care-E-Vac; 2 pages.
One page brochure—Aeros—Moblvacll.
Brochure/Instruction Manual—Creative Medical Laboratories, Inc.—TUGS (Transportable Universal Gradient Suction) System.
Brochure—Wells Johnson Company—Point 5 Aspirator; 2 pages.
Brochure—Microtek Heritage, Inc.—The Wound-Evac ET, Closed Wound Suction System; 4 pages.
Brochure—KCI—The V.A.C. (Vacuum Assisted Closure), Nov. 5, 1998; 7 pages.
Wounds Entiled "Jump-Start Would Healing With Oasis,"vol. 23, No. 2, Apr. 2001.
"Fourth SIS-ECM Symposium," Pointe Hilton Tapatio Cliffs Resort, Phoenix, Arizona, Dec. 6 and 7, 2002.
"Financial News" Section dated Feb. 16, 2000, PR Newswire Association, Inc. (2 pages).
Cook® Online New Release provided by Book Biotech at "www.cookgroup.com", Feb. 16, 2000.
Surgisis™ Soft tissue Repair Biomaterial and Oasis™ Wound Dressing Biomaterial. 2000.
Cook SIS, Products, Oasis™ Wound Dressing, 2000.
Davydov, et al., "Vacuum therapy in the treatment of acute suppurative diseases of soft tissues and suppurative wounds", *Vestn. Khit.*, Sep. 1988, pp. 43-46, and English translation , pp. 1-7.
Davydov, et al., "Pathenogenic mechanism of the effect of vacuum therapy on the course of the wound process", *Khirugiia*, Jun. 1990, pp. 42-47 and English translation, pp. 1-14.

Davydov, et al., "Vacuum therapy in the treatment of suppurative lactation mastitis", *Vestn. Khir.*, Nov. 1986, pp. 66-70 and English translation, pp. 1-13.
Office Action for U.S. Appl. No. 11/242,543, dated Oct. 20, 2006 (8 pages).
Office Action for U.S. Appl. No. 09/855,287, dated Jul. 14, 2005 (10 pages).
Office Action for U.S. Appl. No. 09/855,287, dated Jun. 24, 2004 (9 pages).
Office Action for U.S. Appl. No. 09/855,287, dated Dec. 15, 2003 (7 pages).
Office Action for U.S. Appl. No. 09/855,287, dated Oct. 1, 2002 (9 pages).
"Jump-Start Wound Healing with OASIS", *Wounds*, vol. 13, No. 2, Apr. 2001 (11 pages).
Office Action for U.S. Appl. No. 11/242,543, dated May 18, 2007 (11 pages).
"Healthpoint® OASIS® Wound Matrix", Cook Biotech Incorporated, 2003, (1 page).
United States Securities and Exchange Commission, Kinetic Concepts, Inc., "Form 10-K, Annual Report Pursuant to Section 13 or 15(d) of the Securities Exchange Act of 1934, for the fiscal year ended Dec. 31, 2006,", pp. 1, 2, 3, 12, 13, and 14.
Office Action for U.S. Appl. No. 11/242,543, dated Oct. 25, 2007 (15 pages).
Argenta, Louis C. and Michael J. Morykwas, "Vacuum-Assisted Closure: A New Method for Wound Control and Treatment: Clinical Experience", Annals of Plastic Surgery, vol. 38, No. 6, 1997, pp. 563-576 (14 pages).
Mendez-Eastman, Susan, "When Wounds Won't Heal", RN, Jan. 1998, pp. 20-24 (5 pages).
Greer, S.E, M. Adelman, A. Kasabian, R.D. Galiano, R. Scott and M.T. Longaker, "The use of Subatmospheric Pressure Dressing Therapy to close Lymphocutaneous Fistulas of the Groin", British Journal of Plastic Surgery, 2000, 53, pp. 484-487 (4 pages).
Masters, John, "Reliable, inexpensive and Simple Suction Dressings", Letters to the Editor, British Journal of Plastic Surgery, 1998, vol. 51(3), pp. 267 (1 page).
Letsou, George V., Oscar Rosales, Stacie Maitz, Amy Vogt, Bauer E. Sumpio, "Stimulation of Adenylate Cyclase Activity in Cultured Endothelial Cells Subjected to Cyclic Stretch," Journal of Cardiovascular Surgery, 31, 1990, pp. 634-639 (6 pages).
Blackburn II, James H. et al., "Negative-Pressure Dressings as a Bolster for Skin Grafts; Annal of Plastic Surgery," Lippincott Williams & Wilkins, Inc., Philadelphia, PA, vol. 40 No. 5, May 1998, pp. 453-457 (5 pages).
Brochure "Cavi-Care"; Smith & Nephew Healthcare Limited, 2000, 1 page.
Fleischmann, Dr. W., "Material and Methoden," pp. 489,491-492.
McCarthy, David, "Cook Incorporated Forms Dedicated Tissue Engineered Products Group" Cook Online, News and Media Information, Sep. 2001, pp. 1-2.
SIS Technology, Surgisis, Sep. 2001, pp. 1-4 "Surgisis and Surgisis Es Soft Tissue Graft-Freeze-Dried".
SIS Technology, Surgisis, Sep. 2001, pp. 1-4 "Oasis Wound Dressing Dry Sheet".
Abdullah, "A new method for fixation of drainage catheters," *Journal of Hong Kong College of Radiologists*, 4:272-273, 2001.
Advisory Action issued in U.S. Appl. No. 10/509,137, mailed Jun. 24, 2010.
Advisory Action issued in U.S. Appl. No. 10/885,431, mailed Dec. 8, 2009.
Advisory Action issued in U.S. Appl. No. 11/051,283, mailed May 5, 2010.
Advisory Action issued in U.S. Appl. No. 11/515,983, mailed Feb. 1, 2010.
Advisory Action issued in U.S. Appl. No. 11/761,066, mailed Feb. 16, 2010.
Arnljots and Svedman, "Irrigation Treatment in Split-Thickness Skin Grafting of Intractable Leg Ulcers," *Scand J. Plast Reconstr. Surg.*, 19(2):211-213, 1985.
Bagautdinov, "Variant of external vacuum aspiration in the treatment of purulent diseases of soft tissues," *Current Problems in Modern Clinical Surgery: Interdepartmental Collection*, edited by V. Ye Volkov et al. (Chuvashia State University, Cheboksary, U.S.S.R. 1986);pp. 94-96.
Chinn and Burns, "Closed wound suction drainage," *The Journal of Foot Surgery*, 24(1):76-81, 1985.
Communication of Notice of Opposition issued in European Application No. 07001838.7, mailed Apr. 28, 2010.
Dattilo, Jr. et al.; "Medical textiles: application of an absorbable barbed bi-directional surgical suture"; *Journal of Textile and Apparel, Technology and Management*, 2(2):1-5, 2002.
Davydov et al., "Bacteriological and cytological assessment of vacuum therapy for purulent wounds," *Vestnik Khirurgi*, pp. 48-52 (and 8 page English translation thereof), Oct. 1988.
Davydov et al., "Concepts for the clinical-biological management of the wound process in the treatment of purulent wounds by means of vacuum therapy," *Vestnik Khirurgi*, pp. 132-136 (and 8 page English translation thereof), Jul. 1980.
Davydov et al., "Pathogenic mechanism of the effect of vacuum therapy on the course of the wound process," *Khirurgiia*, (English translation), Jun. 1990.
Davydov et al., "Vacuum Therapy in the Treatment of Purulent Lactation Mastitis," *Vestnik Khirurgi*, pp. 66-70 (and 9 page English translation thereof), May 1986.
Decision on Appeal issued in U.S. Appl. No. 11/242,543, mailed Mar. 5, 2010.
Definition of "pore," provided by Merriam-Webster Online Dictionary, printed Apr. 5, 2010.
Definition of "porous," provided by Merriam-Webster Online Dictionary, printed Apr. 5, 2010.
Egnell Minor, Instruction Book, First Edition, 300, 7502, pp. 24, Feb. 1975.
Egnell Minor: Addition to the Users Manual Concerning Overflow Protection—Concerns all Egnell Pumps, Feb. 3, 1983, pp. 2.
Johnson, "An improved technique for skin graft placement using a suction drain," *Surgery, Gynecology, and Obstetrics*, 159(6):584-585, 1984.
Kuznetsov and Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92, Oct. 1986.
Letter and Memo reporting Office Action issued in Mexican Application No. PA/a/2001/001124, mailed Jul. 13, 2004.
Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
Notice of Allowance issued in U.S. Appl. No. 10/664,535, mailed Jun. 2, 2010.
Notice of Allowance issued in U.S. Appl. No. 10/885,431, mailed Mar. 22, 2010.
Notice of Allowance issued in U.S. Appl. No. 11/761,066, mailed May 13, 2010.
Office Action issued in Australian Application No. 5255/99, mailed Aug. 6, 2002.
Office Action issued in Canadian Application No. 2,338,443, mailed Feb. 7, 2006.
Office Action issued in Canadian Application No. 2,390,131, mailed Jul. 20, 2007.
Office Action issued in Canadian Application No. 2,467,837, mailed May 27, 2009.
Office Action issued in Canadian Application No. 2,481,016, mailed Aug. 13, 2009.
Office Action issued in Canadian Application No. 2,481,016, mailed Jun. 15, 2010.
Office Action issued in Czech Republic Application No. PV2001-497, mailed Feb. 7, 2001.
Office Action issued in European Application No. 00991498.7, mailed Dec. 17, 2003.
Office Action issued in European Application No. 00991498.7, mailed Jan. 2, 2006.
Office Action issued in European Application No. 01998292.5, mailed Feb. 18, 2005.

Office Action issued in European Application No. 01998292.5, mailed Jul. 17, 2006.
Office Action issued in European Application No. 01998292.5, mailed Sep. 12, 2008.
Office Action issued in European Application No. 02784588.2, mailed Sep. 15, 2005.
Office Action issued in European Application No. 08010957.2, mailed Apr. 8, 2009.
Office Action issued in European Application No. 99 937 799, mailed Aug. 18, 2003.
Office Action issued in Japanese Application No. 2001-539532, mailed May 11, 2010 (and English language translation thereof).
Office Action issued in Japanese Application No. 2004-508861, mailed Apr. 14, 2009, and English language translation thereof.
Office Action issued in Japanese Application No. 2004-508861, mailed Feb. 16, 2010 (and English language translation thereof).
Office Action issued in Polish Application No. P-357 417, mailed Nov. 25, 2008; English translation.
Office Action issued in Polish Application No. P-364 754, 2006.
Office Action issued in U.S. Appl. No. 09/369,113, mailed Jan. 31, 2001.
Office Action issued in U.S. Appl. No. 09/725,352, mailed Dec. 12, 2002.
Office Action issued in U.S. Appl. No. 09/743,737, mailed Apr. 1, 2003.
Office Action issued in U.S. Appl. No. 09/743,737, mailed Aug. 11, 2006.
Office Action issued in U.S. Appl. No. 09/743,737, mailed Jun. 19, 2002.
Office Action issued in U.S. Appl. No. 09/743,737, mailed Oct. 23, 2002.
Office Action issued in U.S. Appl. No. 09/743,737, mailed Sep. 8, 2005.
Office Action issued in U.S. Appl. No. 09/994,537, mailed Jan. 16, 2003.
Office Action issued in U.S. Appl. No. 09/994,537, mailed Jun. 30, 2003.
Office Action issued in U.S. Appl. No. 10/144,504, mailed May 14, 2004.
Office Action issued in U.S. Appl. No. 10/267,358, mailed Jun. 29, 2005.
Office Action issued in U.S. Appl. No. 10/496,360, mailed Jun. 2, 2009.
Office Action issued in U.S. Appl. No. 10/496,360, mailed Jun. 12, 2006.
Office Action issued in U.S. Appl. No. 10/496,360, mailed Mar. 14, 2007.
Office Action issued in U.S. Appl. No. 10/496,360, mailed Mar. 26, 2008.
Office Action issued in U.S. Appl. No. 10/496,360, mailed Oct. 3, 2008.
Office Action issued in U.S. Appl. No. 10/496,360, mailed Oct. 5, 2006.
Office Action issued in U.S. Appl. No. 10/496,360, mailed Sep. 10, 2007.
Office Action issued in U.S. Appl. No. 10/496,623, mailed Jun. 9, 2006.
Office Action issued in U.S. Appl. No. 10/509,137, mailed Apr. 9, 2010.
Office Action issued in U.S. Appl. No. 10/509,137, mailed Dec. 20, 2007.
Office Action issued in U.S. Appl. No. 10/509,137, mailed Jan. 10, 2007.
Office Action issued in U.S. Appl. No. 10/509,137, mailed Jun. 3, 2009.
Office Action issued in U.S. Appl. No. 10/509,137, mailed Jun. 22, 2007.
Office Action issued in U.S. Appl. No. 10/509,137, mailed Nov. 24, 2008.
Office Action issued in U.S. Appl. No. 10/524,957, mailed Apr. 11, 2007.
Office Action issued in U.S. Appl. No. 10/524,957, mailed Apr. 15, 2008.
Office Action issued in U.S. Appl. No. 10/524,957, mailed Aug. 3, 2009.
Office Action issued in U.S. Appl. No. 10/524,957, mailed Aug. 10, 2007.
Office Action issued in U.S. Appl. No. 10/524,957, mailed Feb. 25, 2010.
Office Action issued in U.S. Appl. No. 10/524,957, mailed Jul. 26, 2010.
Office Action issued in U.S. Appl. No. 10/524,957, mailed Sep. 30, 2008.
Office Action issued in U.S. Appl. No. 10/664,535, mailed Apr. 2, 2007.
Office Action issued in U.S. Appl. No. 10/664,535, mailed Apr. 17, 2008.
Office Action issued in U.S. Appl. No. 10/664,535, mailed Dec. 15, 2009.
Office Action issued in U.S. Appl. No. 10/664,535, mailed Mar. 1, 2006.
Office Action issued in U.S. Appl. No. 10/664,535, mailed Oct. 16, 2006.
Office Action issued in U.S. Appl. No. 10/664,535, mailed Oct. 26, 2007.
Office Action issued in U.S. Appl. No. 10/885,431, mailed Apr. 15, 2008.
Office Action issued in U.S. Appl. No. 10/885,431, mailed Jun. 24, 2009.
Office Action issued in U.S. Appl. No. 10/885,431, mailed Mar. 22, 2007.
Office Action issued in U.S. Appl. No. 10/885,431, mailed Sep. 11, 2006.
Office Action issued in U.S. Appl. No. 10/885,431, mailed Sep. 19, 2007.
Office Action issued in U.S. Appl. No. 10/885,431, mailed Sep. 26, 2008.
Office Action issued in U.S. Appl. No. 10/997,612, mailed Apr. 30, 2007.
Office Action issued in U.S. Appl. No. 10/997,612, mailed Mar. 20, 2008.
Office Action issued in U.S. Appl. No. 10/997,612, mailed May 5, 2006.
Office Action issued in U.S. Appl. No. 10/997,612, mailed Nov. 14, 2008.
Office Action issued in U.S. Appl. No. 10/997,612, mailed Nov. 19, 2007.
Office Action issued in U.S. Appl. No. 10/997,612, mailed Oct. 31, 2006.
Office Action issued in U.S. Appl. No. 11/051,283, mailed Feb. 22, 2006.
Office Action issued in U.S. Appl. No. 11/051,283, mailed Feb. 25, 2010.
Office Action issued in U.S. Appl. No. 11/051,283, mailed Jan. 9, 2008.
Office Action issued in U.S. Appl. No. 11/051,283, mailed Jun. 5, 2009.
Office Action issued in U.S. Appl. No. 11/051,283, mailed Mar. 22, 2007.
Office Action issued in U.S. Appl. No. 11/051,283, mailed Oct. 17, 2008.
Office Action issued in U.S. Appl. No. 11/051,283, mailed Sep. 7, 2005.
Office Action issued in U.S. Appl. No. 11/051,283, mailed Sep. 7, 2007.
Office Action issued in U.S. Appl. No. 11/051,283, mailed Sep. 29, 2006.
Office Action issued in U.S. Appl. No. 11/230,988, mailed Apr. 16, 2009.
Office Action issued in U.S. Appl. No. 11/230,988, mailed Aug. 26, 2009.
Office Action issued in U.S. Appl. No. 11/230,988, mailed Mar. 13, 2007.
Office Action issued in U.S. Appl. No. 11/230,988, mailed Mar. 26, 2008.

Office Action issued in U.S. Appl. No. 11/230,988, mailed May 26, 2010.
Office Action issued in U.S. Appl. No. 11/230,988, mailed Oct. 3, 2008.
Office Action issued in U.S. Appl. No. 11/230,988, mailed Sep. 10, 2007.
Office Action issued in U.S. Appl. No. 11/230,988, mailed Sep. 28, 2006.
Office Action issued in U.S. Appl. No. 11/347,073, mailed Apr. 1, 2008.
Office Action issued in U.S. Appl. No. 11/515,983, mailed May 7, 2010.
Office Action issued in U.S. Appl. No. 11/515,983, mailed May 11, 2009.
Office Action issued in U.S. Appl. No. 11/515,983, mailed Nov. 20, 2009.
Office Action issued in U.S. Appl. No. 11/684,989, mailed Dec. 29, 2009.
Office Action issued in U.S. Appl. No. 11/684,989, mailed Jul. 7, 2009.
Office Action issued in U.S. Appl. No. 11/684,989, mailed Jun. 29, 2010.
Office Action issued in U.S. Appl. No. 11/684,989, mailed Nov. 18, 2008.
Office Action issued in U.S. Appl. No. 11/761,066, mailed Dec. 9, 2009.
Office Action issued in U.S. Appl. No. 11/761,066, mailed Dec. 13, 2007.
Office Action issued in U.S. Appl. No. 11/761,066, mailed Jun. 2, 2009.
Office Action issued in U.S. Appl. No. 11/761,066, mailed Oct. 28, 2008.
Office Action issued in U.S. Appl. No. 11/761,066, mailed Sep. 25, 2007.
Oosterbroek et al., "A micromachined pressure/flow-sensor," *Sensor and Actuators*, 77(3):167-177, 1999. Abstract Only.
Orringer et al., "Management of wounds in patients with complex enterocutaneous fistulas," *Surgery, Gynecology & Obstetrics*, 165:79-80, 1987.
PCT Declaration of Non-Establishment of International Search Report issued in International Application No. PCT/US2003/17099, mailed Nov. 7, 2003.
PCT International Preliminary Examination Report issued in International Application No. PCT/GB1996/02802, mailed Jan. 15, 1998.
PCT International Preliminary Examination Report issued in International Application No. PCT/US2000/42333, mailed Nov. 19, 2002.
PCT International Preliminary Examination Report issued in International Application No. PCT/US2001/44194, mailed Dec. 3, 2003.
PCT International Search Report issued in International Application No. PCT/GB1995/01983, mailed Nov. 23, 1995.
PCT International Search Report issued in International Application No. PCT/GB1996/02802, mailed Apr. 29, 1997.
PCT International Search Report issued in International Application No. PCT/GB1998/02713, mailed Jan. 8, 1999.
PCT International Search Report issued in International Application No. PCT/US1999/17877, mailed Oct. 27, 1999.
PCT International Search Report issued in International Application No. PCT/US2000/42333, mailed Aug. 3, 2001.
PCT International Search Report issued in International Application No. PCT/US2001/15611, mailed Sep. 5, 2001.
PCT International Search Report issued in International Application No. PCT/US2001/44194, mailed Dec. 9, 2002.
PCT International Search Report issued in International Application No. PCT/US2002/32221, mailed Feb. 5, 2003.
PCT International Search Report issued in International Application No. PCT/US2002/37814, mailed Apr. 7, 2003.
PCT International Search Report issued in International Application No. PCT/US2002/41210, mailed Oct. 28, 2003.
PCT International Search Report issued in International Application No. PCT/US2002/41228, mailed Jun. 30, 2003.
PCT International Search Report issued in International Application No. PCT/US2002/41229, mailed Jun. 30, 2003.
PCT International Search Report issued in International Application No. PCT/US2002/41231, mailed May 9, 2003.
PCT International Search Report issued in International Application No. PCT/US2002/41234, mailed Oct. 24, 2003.
PCT International Search Report issued in International Application No. PCT/US2002/41300, mailed Jul. 31, 2003.
PCT Written Opinion issued in International Application No. PCT/GB1996/02802, mailed Sep. 3, 1997.
PCT Written Opinion issued in International Application No. PCT/GB1998/02713, mailed Jun. 8, 1999.
PCT Written Opinion issued in International Application No. PCT/US1999/17877, mailed Aug. 20, 2001.
PCT Written Opinion issued in International Application No. PCT/US2000/42333, mailed Jun. 24, 2002.
Roget's New Millenium Thesaurus, First Edition (v 1.3.1), 2007.
Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).
Schein et al., "The 'Sandwich Technique' in the management of the open abdomen," *British Journal of Surgery*, 73:369-370, 1986.
Search Report issued in Hungarian Application No. P0103545, mailed Oct. 29, 2001.
Search Report issued in Hungarian Application No. P0500055, mailed May 3, 2005.
Solovev et al., "Guidelines, the method of treatment of immature external fistulas in the upper gastrointestinal tract," editor-in-chief Prov. V.I. Parahonyak, S.M. Kirov Gorky State Medical Institute, Gorky, U.S.S.R., 1987.
Solovev, Dissertation Abstract, "Treatment and prevention of suture failures after gastric resection," S.M. Kirov Gorky State Medical Institute, Gorky, U.S.S.R., 1988.
Supplemental Notice of Allowability issued in U.S. Appl. No. 10/885,431, mailed Apr. 22, 2010.
Supplementary Search Report issued in European Application No. 02794388.5, mailed Jun. 16, 2009.
Supplementary Search Report issued in European Application No. 02794392.7, mailed Jun. 5, 2009.
Supplementary Search Report issued in European Application No. 02794393.5, mailed Aug. 1, 2006.
Supplementary Search Report issued in European Application No. 02794394.3, mailed Apr. 6, 2009.
Supplementary Search Report issued in European Application No. 02794397.6, mailed Jan. 29, 2009.
Supplementary Search Report issued in European Application No. 02796039.2, mailed Sep. 4, 2009.
Supplementary Search Report issued in European Application No. 07001838.7, mailed Mar. 5, 2007.
Supplementary Search Report issued in European Application No. 08010957.2, mailed Aug. 27, 2008.
Svedman et al., "A dressing system providing fluid supply and suction drainage used for continuous or intermittent irrigation," *Annals of Plastic Surgery*, 17(2):125-133, 1986.
Svedman, "A dressing allowing continuous treatment of a biosurface," *IRCS Medical Science: Biomedical Technology, Clinical Medicine, Surgery and Transplantation*, 7:221, 1979.
Tennant, "The use of hypermia in the postoperative treatment of lesions of the extremities and thorax,"*Journal of the American Medical Association*, 64:1548-1549, 1915.
Tribble, "An improved sump drain-irrigation device of simple construction," *Archives of Surgery*, 105(3):511-513, 1972.
Wooding-Scott et al., "No wound is too big for resourceful nurses," *RN*, pp. 22-25, 1988.
Yusupov et al., "Active wound drainage," *Vestnik Khirurgi*, 138(4) (and 7 page English translation thereof), 1987.
Živadinović et al., "Vacuum therapy in the treatment of peripheral blood vessels," *Timok Medical Journal*, 11:161-164 (and copy and certified translation), 1986.
US 6,216,701, 04/2001, Heaton et al. (withdrawn)

* cited by examiner

COMBINATION SIS AND VACUUM BANDAGE AND METHOD

CROSS-REFERENCE TO RELATED APPLICATIONS

This application is a U.S. national counterpart application of international application Ser. No. PCT/US01/15611 filed May 15, 2001, which claims priority to U.S. provisional application Ser. No. 60/206,226 filed May 22, 2000, and is a divisional application of U.S. utility application Ser. No. 09/855,287 filed May 15, 2001.

BACKGROUND OF THE INVENTION

The present invention relates to wound care and more particularly to the provision of an SIS wound care cover used in combination with a vacuum bandage. The invention contemplates both apparatus and a method for using the apparatus.

It is known to use small intestine submucosa (SIS) in wound care treatment, particularly the application of layers of SIS directly upon an open wound that has been debrided and cleaned. SIS is described in the following U.S. Pat. Nos.: 5,855,619, 5,866,414, 5,753,267, 5,762,966, 5,755,791, 4,902,508, 4,956,178, 5,275,826, 5,281,422, 4,352,463, 5,372,821, 5,445,833, 5,516,533, 5,573,784, 5,645,860, 5,641,518, 5,711,969, and 5,695,998. These patents disclose the nature of SIS.

SIS has been described as a natural acellular biomaterial used to repair, support, and stabilize a wide variety of anatomical defects and traumatic injuries. See, for example, the COOK® Online New Release provided by Cook Biotech and submitted in the Information Disclosure Statement filed concurrently with the present patent application. The SIS material is a tissue engineered collagen matrix derived from porcine small intestinal submucosa that models the qualities of its host when implanted in human soft tissues. Further, it is taught that the SIS material provides a natural scaffold-like matrix with a three-dimensional structure and biochemical composition that attracts host cells and supports tissue remodeling. SURGISIS™ Soft Tissue Repair Biomaterial and OASIS™ Wound Dressing Biomaterial are available for remodeling partial thickness skin injuries (Cook Biotech, Bloomington, Ind.). The OASIS™ Wound Dressing is provided in single thickness, fenestrated sheets. It will be appreciated that SIS is readily available for use as a wound dressing.

While small intestine submucosa is available, other sources of submucosa are known to be effective for tissue remodeling. These sources include, but are not limited to, stomach, bladder, alimentary, respiratory, or genital submucosa. See, e.g., U.S. Pat. Nos. 6,171,344, 6,099,567, and 5,554,389. Further, it is known that these various submucosa materials may be derived from non-porcine sources, including bovine and ovine sources. Additionally, other collagen matrices are known, for example lamina propria and stratum compactum.

It is also known to use a vacuum treatment bandage for accelerating wound healing. A vacuum bandage is a bandage having a cover for sealing about the outer perimeter of the wound and under which a vacuum is established to act on the wound surface. This vacuum applied to the wound surface accelerates healing of chronic wounds. Typically, suction tubes are provided for drawing exudate away from the wound, and the suction tubes may be used to create the vacuum under the cover. If the cover is a flexible cover, which is typically more comfortable for the patient, a porous packing may be provided under the cover to provide the space in which the vacuum is formed. Additionally, it is known a heater within a wound treatment apparatus to promote healing. The following U.S. patents establish the nature of vacuum and/or heat treatment bandages and devices: U.S. Pat. Nos. 6,095,992, 6,080,189, 6,071,304, 5,645,081, 5,636,643, 5,358,494, 5,298,015, 4,969,880, 4,655,754, 4,569,674, 4,382,441, and 4,112,947.

As shown, for example, in U.S. Pat. No. 5,645,081 (hereinafter the '081 patent), a method of treating tissue damage is provided by applying negative pressure to a wound. The negative pressure is provided in sufficient duration and magnitude to promote tissue migration in order to facilitate the closure of the wound. FIG. 1 of the '081 patent discloses an open cell polyester foam section covering the wound, a flexible hollow tube inserted into the foam section at one end and attached to a vacuum pump at another end, an adhesive sheet overlying the foam section, and tubing to adhere to the skin surrounding the wound in order to form a seal that allows the creation of a vacuum when the suction pump is operating. The '081 patent further teaches use of negative pressure between about 0.1 and 0.99 atmospheres, and that the pressure can be substantially continuous, wherein the pressure is relieved only to change the dressing on the wound. Alternatively, the '081 patent teaches use of a cyclic application of pressure in alternating periods of application and non-application. In a preferred embodiment, pressure is applied in 5 minute periods of application and non-application.

The following pending applications, assigned to the same assignee as the present application is licensed, are also related to the use of vacuum to promote healing: U.S. patent application Ser. No. 09/369,113 filed Aug. 5, 1999, and titled Wound Treatment Apparatus, U.S. patent application Ser. No. 09/725,352 filed Nov. 29, 2000, and titled Vacuum Therapy and Cleansing Dressing for Wounds, and U.S. patent application Ser. No. 09/725,666 filed Nov. 29, 2000, and titled Wound Treatment Apparatus.

Various of prior art references teach the value of the vacuum bandage or the provision of vacuum to the surface of a chronic wound. Several Russian language articles exist that establish the efficacy of vacuum therapy. Examples of such prior art articles, each of which discusses the use of application of vacuum to a wound to promote healing, are as follows: *Vacuum therapy in the treatment of acute suppurative diseases of soft tissues and suppurative wound*, Davydov, et al. Vestn. Khir., September 1988 ("the September 1988 article"); *Pathenogenic mechanism of the effect of vacuum therapy on the course of the wound process*, Davydov, et al. Khirurigiia, June 1990 ("the June 1990 article"); and *Vacuum therapy in the treatment of suppurative lactation mastitis*, Davydov, et al., Vestn. Khir., November 1986 ("the November 1986 article").

The Russian articles distinguish wound drainage from use of vacuum therapy for healing, and they report that vacuum therapy results in faster cleansing of the wound and more rapid detoxification than with the traditional incision-drainage method. The November 1986 article describes the vacuum therapy protocol as 0.8-1.0 atmosphere for 20 minutes at the time of surgery, and subsequent 1.5 to 3 hour treatments at a vacuum of 0.1 to 0.15 atmosphere, twice daily. These Russian articles teach that use of negative pressure accelerates healing. The Russian articles further teach using this vacuum method to decrease the number of microbes in the wound. The June 1990 article teaches that vacuum therapy provides a significant antibacterial effect. The June 1990 article describes the stepped up inflow of blood to the zone around the wound, which leads to an increase in the number of leukocytes reaching the focus of inflamation. Moreover, the Russian articles teach improvement of local blood circulation using vacuum therapy. The September 1988 article teaches improved inflow of blood into the wound zone, which intensifies the repair processes. The June 1990 article teaches that vacuum therapy promotes mobilization of blood plasma, intertissue fluid, and lymph into the wound. The June 1990 article reports that cellular and non-cellular elements of connective tissue appear twice as quickly in wounds treated with vacuum therapy. Subsequent articles and patents further develop the benefits obtained with vacuum therapy. The prior art, therefore, teaches the benefit and value of a vacuum bandage.

SUMMARY OF THE INVENTION

According to the present invention, a wound care bandage is provided that combines the advantages of SIS and vacuum therapy to control and enhance the flow of fluid from the wound bed and into the SIS material. The present invention, therefore, is a method for controllably drawing fluid from the surrounding tissue and into an SIS layer placed on the wound, thereby enhancing the healing and restructuring properties of the SIS.

The present invention comprises structure to provide a space above the SIS and the wound bed, in which space a vacuum is developed to cause blood flow from the wound bed into the SIS. Furthermore, the method contemplates controlling the vacuum level and the application time of the vacuum to present optimum blood flow from the wound bed into the SIS.

In preferred embodiments, the wound care bandage includes an SIS layer to be placed in contact with the wound bed. As mentioned above, the wound care bandage further includes a structure placed over the SIS layer to provide a vacuum space between the SIS layer and a cover placed over the structure and SIS layer. The cover is coupled to the patient's skin surrounding the wound to provide a sealed environment. A vacuum source is coupled to the wound covering for communication with the vacuum space created by the structure. The vacuum source is used to create a vacuum within the sealed environment in order to draw blood from the wound bed up through the SIS layer to promote the healing process. The vacuum suction is to be at a level sufficient to draw blood to the SIS layer, for example, 125 mm Hg. It will be appreciated, however, that varying levels of vacuum suction and varying protocols for the duration of application of vacuum are within the scope of the present invention.

In further embodiments, the space-providing structure is a porous or reticulated pad or other structure having air passageways extending from the SIS layer to the cover. In still further embodiments, the space-providing structure may be a foam ring, or it may be the cover itself, provided that the cover is sufficiently rigid.

Thus, in one aspect of this invention a wound care bandage is provided comprising a collagen matrix formed for placement on a wound, a cover configured for placement over the wound to provide a sealed environment around the wound and adapted for communication with a vacuum source, and a structure for placement between the collagen matrix and the cover and configured to provide a vacuum space. In preferred embodiments, the collagen matrix is a layer of submucosa.

In another aspect of this invention a wound care bandage is provided comprising an SIS layer adapted to be placed on a wound, and a cover configured to be placed over the wound and the SIS layer to provide a vacuum space between the SIS layer and an inside surface of the cover, the space-being connectable with a vacuum source.

Still another aspect of this invention includes a method for promoting wound healing comprising the steps of providing a wound care bandage having an SIS layer adapted to be placed on a wound, a cover to be placed over the wound to provide a vacuum space above the wound, a structure to define the vacuum space between the SIS layer and the cover, and creating a vacuum within the vacuum space to controllably draw blood from the wound into the SIS layer placed over the wound.

Yet another aspect of this invention is directed to a method for promoting wound healing comprising the steps of applying an SIS layer to a wound surface, placing a support structure over the SIS layer, placing a cover over the wound, SIS layer and support structure to define a vacuum space, connecting the cover to a vacuum source, and creating a vacuum within the vacuum space.

An additional aspect of this invention is directed to a method for promoting wound healing comprising the steps of applying a collagen matrix to a wound surface, creating a vacuum space in communication with the wound and the collagen matrix, and generating a vacuum within the vacuum space in a magnitude and duration sufficient to draw blood from the wound into the collagen matrix.

A final aspect of this invention is a kit for promoting wound healing, the kit comprising a submucosa layer for contacting the wound, a porous pad, and a cover for creating a seal around the wound and configured for communication with a vacuum source.

BRIEF DESCRIPTION OF THE DRAWINGS

The detailed description particularly refers to the accompanying figures in which.

DETAILED DESCRIPTION OF THE DRAWINGS

Figure 1:
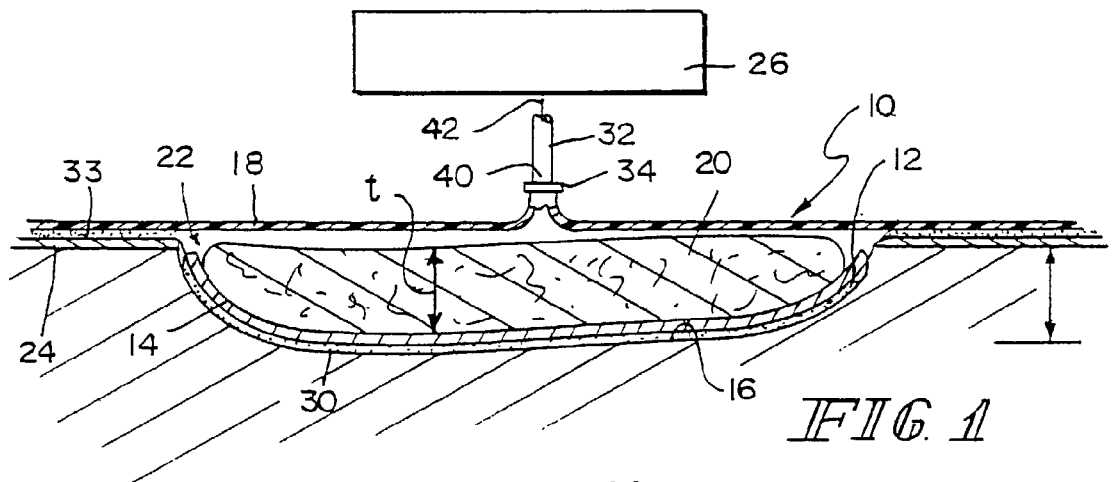
FIG. 1 is a sectional view of a debrided wound and a wound care bandage showing an SIS layer, a porous pad or filler, and a cover of the wound care bandage, and further showing the cover of the wound care bandage in communication with a tube adapted to lead to a vacuum source.
Figure 2:
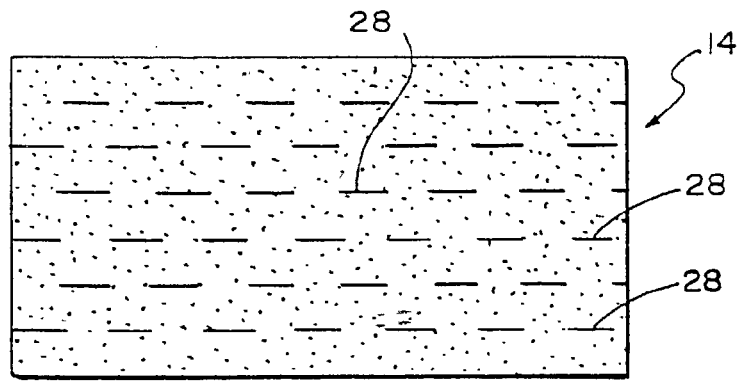
FIG. 2 is a plan view of the SIS layer shown in FIG. 1 showing fenestrations in the SIS layer.

A wound care bandage 10 is provided, as shown in FIGS. 1-5, for use with a debrided wound 12. Referring to FIG. 1, bandage 10 includes a small intestinal submucosa (SIS) layer 14 which lies adjacent to a wound surface 16 of wound 12. Bandage 10 further includes a cover 18 for placement over wound 12 and a structure 20, 120, 220, or 320 positioned between SIS layer 14 and cover 18 in order to create a vacuum space 22. Cover 18 is coupled to a portion of the patient's skin 24 surrounding wound 12 in order to enclose wound 12, SIS layer 14, and structure 20, 120, 220, or 320 within a sealed environment. Bandage 10 further includes a means for communicating vacuum space 22 with a vacuum source 26. The wound care bandage 10, therefore, combines the healing properties of the SIS layer 14 with the acceleration provided by the vacuum therapy.

SIS layer 14, which is applied directly to wound surface 16, may be fenestrated (or perforated) to prevent fluid accumulation below the SIS layer 14. Such fenestrations 28 are shown, for example, in FIG. 2. Equipment is available for fenestrating skin grafts and it is contemplated that such equipment could also be used to fenestrate SIS layer 14. These fenestrations 28, or perforations, in the SIS layer 14 permit blood from the wound 12 to migrate upwardly into the SIS layer 14 and deposit cells to start the tissue growth in the SIS framework of the SIS layer 14.

Further, SIS layer 14 may be formed to include one single sheet of SIS or multiple sheets of SIS. For SIS layer 14 including multiple SIS sheets, the sheets may be positioned in any number of orientations relative to each other. It is further within the scope of the disclosure for SIS layer 14 to have any reasonable thickness for its use in bandage 10. It is also known in the art that larger sheets of submucosa may be formed by fusing multiple strips of submucosa tissue. See U.S. Pat. No. 5,711,969. In a preferred embodiment, SIS layer 14 is sized to fit the wound and is flexible in order to allow the SIS layer 14 to conform to any complex wound or wound surface. Additionally, it is known to treat wounds with SIS provided in fresh, frozen, or lyophilized forms. Lyophilized SIS may be used in the dried form, or it may be hydrated prior to use.

In some optional embodiments, a biological glue 30 is provided between the debrided wound surface 16 and the SIS layer 14 in order to hold the SIS layer 14 in a stationary position against the wound surface 16, as shown, for example, in FIG. 1. One type of biological glue 30 used may be a fibrin sealant, for example. It is within the scope of this disclosure, however, to include any type of biological glue sufficient for holding the SIS layer 14 stationary relative to wound surface 16.

SIS is intended to identify porcine small intestine submucosa. While reference is made herein to SIS, it will be appreciated that small intestine submucosa may be obtained from other animal sources, including cattle, sheep, and other warm-blooded mammals. Further, other sources of submucosa from various tissue are known to be effective for tissue remodeling as well. These sources include, but are not limited to, stomach, bladder, alimentary, respiratory, and genital submucosa. Such submucosa-derived matrices comprise highly conserved collagens, glycoproteins, proteoglycans, and glycosaminoglycans. Additionally, other collagen matrices are known that can act as a biological scaffolds. Thus, it is understood that while the preferred embodiment uses SIS, other collagen matrices may be used within the scope of this invention.

The structure of bandage 10, is provided to form vacuum space 22 between SIS layer 14 and cover 18. A structure supports cover 18 while providing air passageways to the wound surface 16 and the SIS layer 14. As shown in FIG. 1, the structure is preferably a reticulated or porous filler or pad 20 having airflow passageways (not shown) extending throughout pad 20. It is preferred that pad 20 be rather flexible to conform to any complex wound or wound surface and to be comfortable for the patient. Further, it is preferred that the thickness of the structure is selected to provide proper vacuum access to all parts of the wound to be served. It is further preferred that a thickness, t, of the reticulated flexible pad 20 be approximately one to two centimeters. The reticulated or porous pad 20 may be cut by the surgeon to be larger than the SIS layer 14 and even larger than the wound 12.

Figure 3:
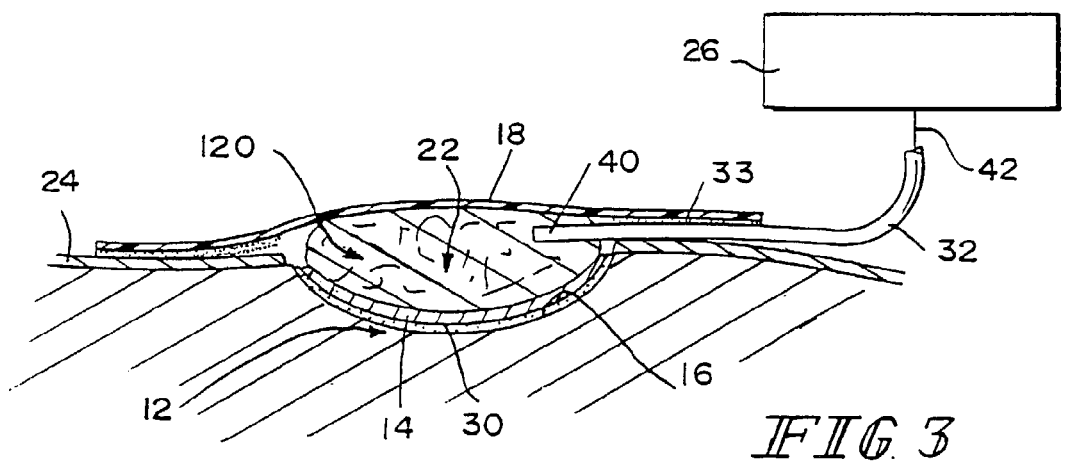
FIG. 3 is a sectional view of another debrided wound and another wound care bandage including an SIS layer, a walled structure to provide a vacuum space, a covering, and a vacuum tube positioned to lie under the cover and in communication with the vacuum space at one end and a vacuum source an another end.
Figure 4:
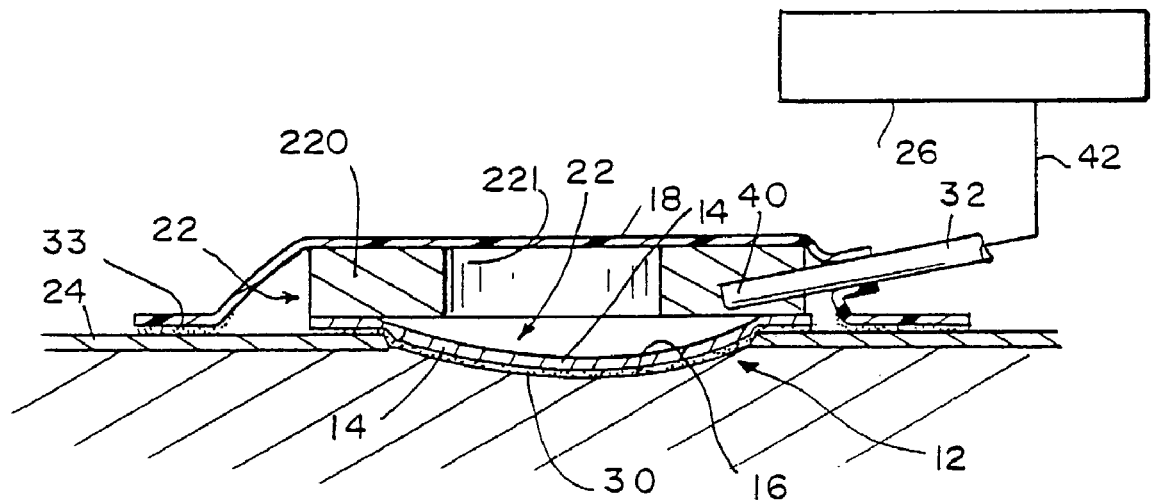
FIG. 4 is a sectional view of another embodiment of the present invention showing another wound care bandage over a debrided wound and showing the bandage including an SIS layer, a ring-shaped structure defining a vacuum space in communication with the vacuum source, and a cover positioned over the structure.

Although porous pad 20 has been described above, it is within the scope of this disclosure to include any such structure which functions to create a space between the SIS layer 14 and the cover 18 and permits air flow from the wound 12 to transmit negative pressure to the wound surface 16. As shown in FIG. 3, the structure 120 may be gauze, or, as shown in FIG. 4, the structure may be a foam ring 220 or other such ring to position cover 18 in spaced-apart relation to SIS layer 14. Ring 220 includes an aperture defined by an inner wall 221 of the ring 220. The vacuum space 22 is thus defined by the SIS layer 14, the cover 18, and the inner wall 221 of ring 220.

Figure 5:
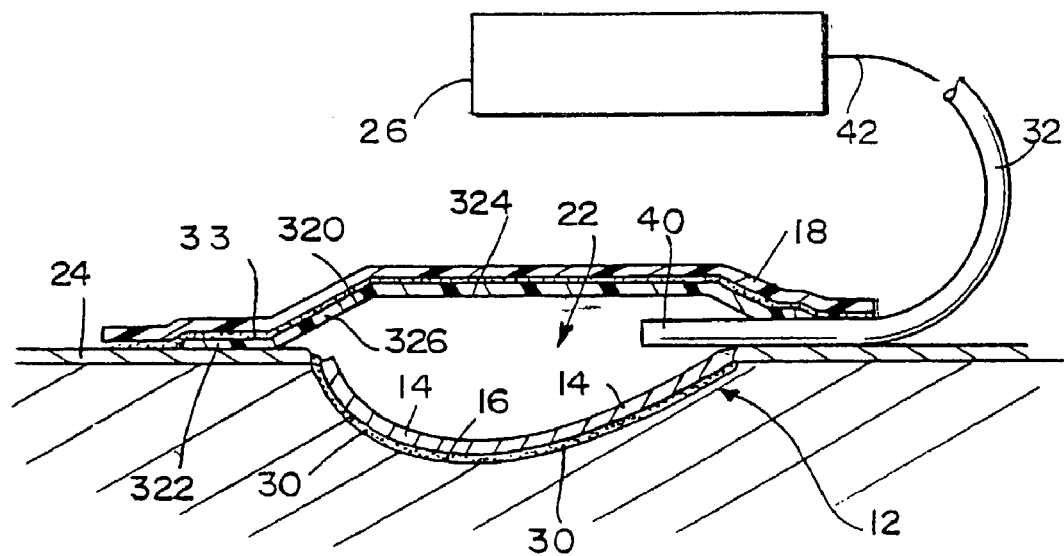
FIG. 5 is a sectional view of another embodiment of the present invention showing the bandage including a semi-rigid walled structure for defining a vacuum space in communication with the vacuum source.

Further, as shown in FIG. 5, for example, the structure may be a rigid dome or a preferably semi-rigid dome 320 which supports the cover 18 above the SIS layer 14. Semi-rigid dome 320 includes a lower member 322 adapted to lie adjacent the patient's skin surrounding wound 12, an upper member 324 normally spaced-apart from SIS layer 14, and a middle member 326 for supporting the upper member 324 in spaced-apart relationship with the SIS layer 14. Semi-rigid dome 320 may be generally dome-shaped, for example, as well. Although such examples as porous pad 20, foam ring 220, and semi-rigid dome 320 have been provided as examples for the structure, it is within the scope of this disclosure for bandage 10 to include any space providing structure above the SIS layer 14 and below the cover 18 for communication with a vacuum service 26.

Cover 18 of the bandage 10 lies over the space-providing structure to fully enclose the structure, SIS layer 14, and wound 12. Cover 18 is coupled to the patient's skin 24 which surrounds the wound 12. For example, cover 18 may be a thin transparent, non-porous adhesive sheet to adhere to the surface of the skin 24 about the wound 12 to provide a vacuum enclosure. An adhesive 33 for coupling cover 18 to skin 24 is shown in FIGS. 1 and 3-5. A product such as Tegaderm™ (3M Health Care Ltd., (St. Paul, Minn.)) would be suitable for the cover, for example. It is within the scope of this disclosure, however, to include any suitable non-porous impermeable or semi-permeable sheet. While a flexible or semi-rigid sheet is preferred for patient comfort, a rigid cover, such as a glass dome, is within the scope of this invention. When a rigid cover is used, a separate space-providing structure is not needed, as the rigid cover may be configured to provide the vacuum space.

In order to encourage blood flow to the wound 12 and wound surface 16, vacuum space 22 of wound care bandage 10 is connected with vacuum source 26. A vacuum tube 32 may be provided, for example, for fluid communication with vacuum space 22 and vacuum source 26. As shown in FIG. 1, vacuum tube 32 is coupled to cover 18 and in communication with vacuum space 22. A first end 40 of tube 32 includes a collar 34 coupled to an aperture of the cover 18. As shown diagrammatically, a second end 42 of tube 32 is coupled to vacuum source 26.

In other embodiments, as shown in FIGS. 3-5, for example, tube 32 is placed under cover 18 and into vacuum space 22. Cover 18 is sealed around tube 32 in order create a sealed environment for the vacuum to function properly. The vacuum may be provided by a suction tube disposed in the space and configured to draw excess wound drainage away from the wound. Another type of fluid connection system between a wound dressing and a vacuum source is disclosed in U.S. Pat. No. 4,969,880. Furthermore, while first end 40 of tube 32 is shown in FIGS. 3 and 4 as being located in the structure 120 or 220, it is understood that first end 32 may be placed directly on the SIS layer 14. Additionally, it is understood that tube 32 may be a Jackson-Pratt type drain, with holes distributed along its length adjacent first end 32.

The vacuum may be provided in vacuum space 22 for controlled periods of time. For example, initially, the vacuum may be applied for a sufficient time to draw blood into the SIS layer 14, such as up to 125 mm Hg, for example. It will be appreciated that this invention contemplates developing different protocols for amounts of vacuum and application times. It will also be appreciated that the vacuum may be provided by a perforated tube positioned and configured to carry away excess wound drainage.

In treating wound 12, a caretaker first cleans and prepares the wound surface 16. Once wound surface 16 is prepared, bandage 10 is to be applied to the wound. SIS layer 14 is positioned over the wound 12 to cover the prepared wound surface 16. Structure 20, 120, 220, or 320 is placed over the SIS layer 14 to define the vacuum space and cover 18 is placed over the wound 12, SIS layer 14, and structure 20. Cover 18 is connected to a vacuum source 26. Finally, suction is applied to the vacuum space 22 in sufficient magnitude and duration to draw blood from the wound into the SIS layer 14. Optionally, a biological glue 30 may be placed on the wound surface 16 prior to application of the bandage 10.

Vacuum may be applied at any magnitude or duration to promote inflow of blood from the wound into the layer of SIS. Preferably, vacuum may be applied from 0.1 to 0.99 atmospheres, and more preferably 0.1 to 0.15 atmospheres. In one embodiment, vacuum is applied essentially continuously until healing takes place. In another embodiment, vacuum is used in periods of application and non-application, and the structure and cover may be removed during periods of non-application. These alternating periods may include one or two periods of application each day for several days. In another embodiment, the negative pressure is applied in 5 minute periods of application and non-application.

It is known that SIS can be integrated into the wound and restructured to resemble the surrounding tissue. Thus, while the magnitude and duration of application of vacuum may vary, in a preferred embodiment the SIS remains on the surface of the wound for the duration of treatment. In optional embodiments, additional layers of SIS may be added as the SIS is integrated into the wound. The additional layers may be smaller pieces to be placed on localized areas of integration, or, because the vacuum promotes blood flow into the SIS layer, may be full size pieces conforming to the size of the wound surface.

Thus, in one embodiment the present invention is a method for treating wounds comprising the steps of preparing the wound surface, applying a bandage to the wound, the bandage having an SIS layer secured over the wound and a cover above the wound and the SIS layer to define a vacuum space between the wound and SIS layer, and applying suction to the vacuum space to draw blood from the wound into the SIS layer.

Although this invention has been described in detail with reference to certain embodiments, variations and modifications exist within the scope and spirit of the invention as described and defined in the following claims.

The invention claimed is:

1. A method for promoting wound healing, the method comprising:
    applying a first small intestine submucosa (SIS) layer to a wound surface,
    creating a vacuum space in communication with the wound and the first SIS layer by placing a cover over the SIS layer,
    generating a vacuum within the vacuum space in a magnitude and duration sufficient to draw blood from the wound into the first SIS layer, wherein no sutures and no stapes are used to hold the SIS layer in place during communication of negative pressure to the vacuum space by the vacuum source,
    wherein creating the vacuum space includes positioning a structure between the first SIS layer and the cover to provide the vacuum space, and
    wherein the structure comprises a ring having an aperture defined by an inner wall of the ring and wherein the vacuum space is defined by the first SIS layer, the cover, and the inner wall of the ring.

2. The method of claim 1, wherein the vacuum is generated in periods of application and non-application.

3. The method of claim 1, wherein the SIS layer includes one or more sheets of SIS.

4. The method of claim 1, wherein the SIS layer is fenestrated.

5. The method of claim 1, wherein the vacuum is generated for a sufficient period of time to begin integration of the first SIS layer into the wound surface, and further comprising the step of placing a second SIS layer over the first SIS layer.

6. The method of claim 1, wherein the ring comprises foam.

7. The method of claim 1, wherein the wherein the ring has a thickness of approximately 1-2 centimeters.

8. The method of claim 1, wherein the vacuum is generated with a vacuum source coupled to the cover by a vacuum tube.

9. The method of claim 1, wherein the vacuum is generated at a constant rate to controllably draw blood from the wound into the SIS layer.

10. The method of claim 1, wherein generating the vacuum includes generating a vacuum of about 0.1 to about 0.15 atmospheres.

* * * * *

UNITED STATES PATENT AND TRADEMARK OFFICE
CERTIFICATE OF CORRECTION

PATENT NO. : 7,910,791 B2  Page 1 of 1
APPLICATION NO. : 10/276778
DATED : March 22, 2011
INVENTOR(S) : Arthur C. Coffey It is certified that error appears in the above-identified patent and that said Letters Patent is hereby corrected as shown below:

In title page, item (56) References Cited - U.S. PATENT DOCUMENTS, insert
--4,139,004   2/1979   Gonzalez Jr.
4,605,399   8/1986   Weston et al.
4,717,382   1/1988   Clemens et al.
4,962,761   10/1990   Golden
5,014,389   5/1991   Ogilvie et al.
5,176,667   1/1993   DeBring
5,549,584   8/1996   Gross
2004/0030304   2/2004   Ingman--.

In title page, item (56) References Cited - FOREIGN PATENT DOCUMENTS, delete
"JP     4-129436        4/1992" and insert
--JP     4-129536        4/1992-- therefor.

Signed and Sealed this
Twenty-first Day of February, 2012

David J. Kappos
*Director of the United States Patent and Trademark Office*